(12) United States Patent
Gabelberger et al.

(10) Patent No.: US 12,011,199 B2
(45) Date of Patent: Jun. 18, 2024

(54) BONE PLATE, BONE PLATE SYSTEM, AND METHOD OF USING THE SAME

(71) Applicant: DEPUY SYNTHES PRODUCTS, INC., Raynham, MA (US)

(72) Inventors: Josef Gabelberger, West Chester, PA (US); David Cowens, West Chester, PA (US); Joshua McManus, Downingtown, PA (US); Thomas Keyer, West Chester, PA (US); Catherine Santis, Warsaw, IN (US); Robert Khatchadourian, Lafayette Hill, PA (US); Peter Van Citters, Phoenixville, PA (US); David W. Bogle, Coatsville, PA (US); Alexandra Sibole, Seattle, WA (US)

(73) Assignee: DePuy Synthes Products, Inc., Raynham, MA (US)

( * ) Notice: Subject to any disclaimer, the term of this patent is extended or adjusted under 35 U.S.C. 154(b) by 628 days.

(21) Appl. No.: 17/071,669

(22) Filed: Oct. 15, 2020

(65) Prior Publication Data
US 2022/0117639 A1 Apr. 21, 2022

(51) Int. Cl.
*A61B 17/80* (2006.01)
*A61B 17/72* (2006.01)
*A61B 17/88* (2006.01)

(52) U.S. Cl.
CPC ........ *A61B 17/8085* (2013.01); *A61B 17/808* (2013.01); *A61B 17/8863* (2013.01);
(Continued)

(58) Field of Classification Search
CPC ............ A61B 17/8061; A61B 17/8014; A61B 17/808; A61B 17/8052; A61B 17/746;
(Continued)

(56) References Cited

U.S. PATENT DOCUMENTS

| 4,398,322 A | 8/1983 | Ewen |
| 5,122,146 A | 6/1992 | Chapman et al. |

(Continued)

FOREIGN PATENT DOCUMENTS

| CN | 203619652 A1 | 6/2014 |
| CN | 203935262 U | 11/2014 |

(Continued)

OTHER PUBLICATIONS

DePuy Synthes, Titanium Cannulated Retrograde/Antegrade Femoral Nail, Surgical Technique, Jun. 2017, 81 pages.
(Continued)

*Primary Examiner* — Marcela I. Shirsat
(74) *Attorney, Agent, or Firm* — BakerHostetler

(57) ABSTRACT

A bone plate comprises a plate body and at least one tab. The plate body defines an inner body surface configured to face an underlying bone, an outer body surface opposite the inner body surface, and an outer side surface that extends between the inner body surface and the outer body surface. The outer side surface defines an outer perimeter of the plate body. The at least one tab includes a head and an arm that extends from the plate body to the head. The tab defines a tab aperture that extends through the head and is configured to receive a bone anchor. The bone anchor can be coupled with a screw hole in the nail. The arm is configured to deflect with respect to the plate body so as to move the head between a pre-fixation position and a fixation position spaced from the pre-fixation position.

17 Claims, 18 Drawing Sheets

(52) U.S. Cl.
CPC ....... *A61B 17/7233* (2013.01); *A61B 17/8014* (2013.01); *A61B 17/8052* (2013.01)

(58) Field of Classification Search
CPC ............ A61B 17/8085; A61B 17/8863; A61B 17/7233
USPC ................... 606/70, 281, 291, 64; 623/21.18
See application file for complete search history.

(56) References Cited

U.S. PATENT DOCUMENTS

| | | | |
|---|---|---|---|
| 5,207,682 | A | 5/1993 | Cripe |
| 5,620,456 | A | 4/1997 | Sauer et al. |
| 5,704,941 | A | 1/1998 | Jacober et al. |
| 6,126,359 | A | 10/2000 | Dittrich et al. |
| 6,258,095 | B1 | 7/2001 | Lombardo et al. |
| 6,783,529 | B2 | 8/2004 | Hover et al. |
| 7,131,974 | B2 | 11/2006 | Keyer et al. |
| 7,357,804 | B2 | 4/2008 | Binder, Jr. et al. |
| 7,549,994 | B2 | 6/2009 | Zander et al. |
| 7,618,420 | B2 | 11/2009 | Collazo |
| 7,621,921 | B2 | 11/2009 | Parker |
| 8,080,015 | B2 | 12/2011 | Buttler et al. |
| 8,337,533 | B2 | 12/2012 | Raines et al. |
| 8,361,077 | B2 | 1/2013 | Keller |
| 8,486,072 | B2 | 7/2013 | Haininger |
| 8,668,694 | B2 | 3/2014 | Teeny |
| 8,753,343 | B2 | 6/2014 | Staeubli |
| 8,764,752 | B2 | 7/2014 | Buettler et al. |
| 9,066,764 | B2 | 6/2015 | Perez |
| 9,204,912 | B2 | 12/2015 | Price et al. |
| 9,308,004 | B2 | 4/2016 | Giersch et al. |
| 9,393,064 | B2 | 7/2016 | Roethlisberger et al. |
| 9,439,780 | B2 | 9/2016 | Witt et al. |
| 9,463,053 | B2 | 10/2016 | Garino |
| 9,463,054 | B2 | 10/2016 | Mueckter |
| 9,968,389 | B2 | 5/2018 | Garino |
| 9,993,267 | B2 | 6/2018 | Orsak et al. |
| 10,206,724 | B2 | 2/2019 | Williams |
| 10,258,402 | B2 | 4/2019 | Silva et al. |
| 10,327,824 | B2 | 6/2019 | Ricker et al. |
| 10,765,462 | B2 | 9/2020 | Penman et al. |
| 11,413,078 | B2 | 8/2022 | Penman et al. |
| 2003/0135212 | A1 | 7/2003 | Y. Chow |
| 2006/0235400 | A1* | 10/2006 | Schneider .......... A61B 17/8052 606/291 |
| 2009/0177240 | A1 | 7/2009 | Perez |
| 2009/0204121 | A1* | 8/2009 | Cavallazzi ......... A61B 17/1739 606/80 |
| 2010/0106196 | A1 | 4/2010 | Erickson et al. |
| 2010/0217327 | A1 | 8/2010 | Vancelette et al. |
| 2010/0256685 | A1* | 10/2010 | Plecko ............... A61B 17/8061 606/281 |
| 2011/0190769 | A1* | 8/2011 | Haininger .......... A61B 17/8061 606/64 |
| 2011/0264149 | A1 | 10/2011 | Pappalardo et al. |
| 2014/0094821 | A1 | 4/2014 | Wagner et al. |
| 2014/0107798 | A1* | 4/2014 | Jeng .................... A61B 17/808 623/21.18 |
| 2014/0378973 | A1* | 12/2014 | Mueckter ............. A61B 17/746 606/64 |
| 2015/0366593 | A1* | 12/2015 | Mebarak ............ A61B 17/8014 606/281 |
| 2016/0175112 | A1 | 6/2016 | Pruvost et al. |
| 2017/0056081 | A1 | 3/2017 | Langdale et al. |
| 2019/0133651 | A1 | 5/2019 | Williams |
| 2019/0262046 | A1 | 8/2019 | Ricker et al. |
| 2020/0214751 | A1 | 7/2020 | Sixto et al. |
| 2022/0031340 | A1 | 2/2022 | Dogu et al. |

FOREIGN PATENT DOCUMENTS

| | | |
|---|---|---|
| EP | 1398000 B1 | 8/2006 |
| EP | 1398001 B1 | 8/2008 |
| EP | 2030596 A1 | 3/2009 |
| EP | 2349039 B1 | 9/2009 |
| EP | 3122290 B1 | 8/2019 |
| IN | 201003084 A | 11/2010 |
| WO | 2011017066 A1 | 2/2011 |
| WO | 2015144772 A1 | 10/2015 |
| WO | 2017198748 A1 | 11/2017 |
| WO | 2018072181 A1 | 4/2018 |
| WO | 2020/168092 A1 | 8/2020 |

OTHER PUBLICATIONS

Interprosthetic and Peri-Implant Fractures: Principles of Operative Fixation and Future Directions, by Liporace et al., J Orthop Trauma, vol. 31, No. 5, May 2017, pp. 287-292. (www.jorthotrauma.com).
Nail Plate Combination (NPC) Technique for Native and Periprosthetic Distal Femur Fractures a Technical Trick, Journal of Orthopaedic Trauma Publish Ahead of Print—DOI: 10.1097/BOT.0000000000001332, Liporace et al., pp. 1-26.
Intramedullary Nail and Plate Combination Fixation for Complex Distal Tibia Fractures: When and How? By Yoon et al., J Orthop Trauma, vol. 30, No. 11 Supplement, Nov. 2016 pp. S17-S21 (www.jorthotrauma.com).

* cited by examiner

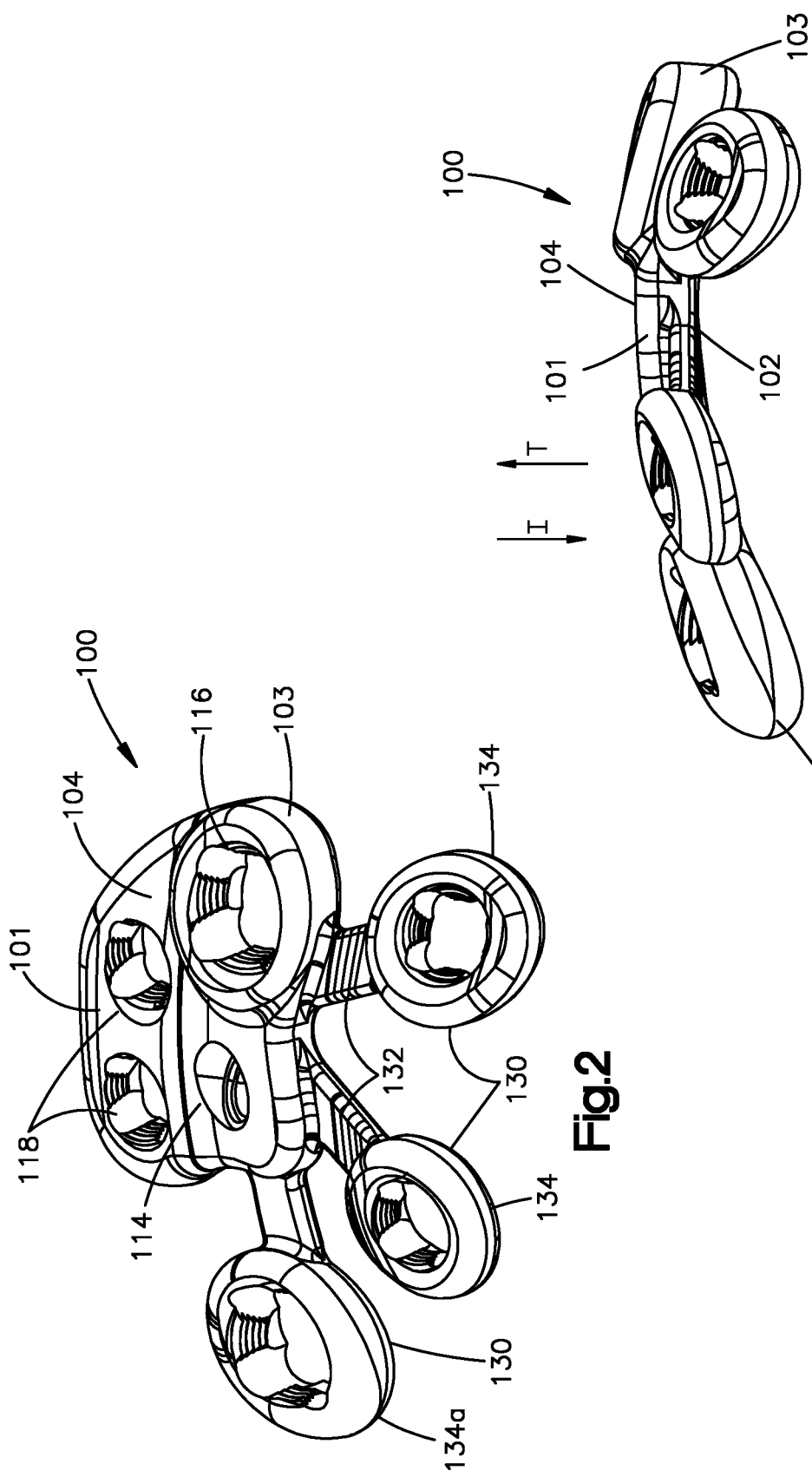

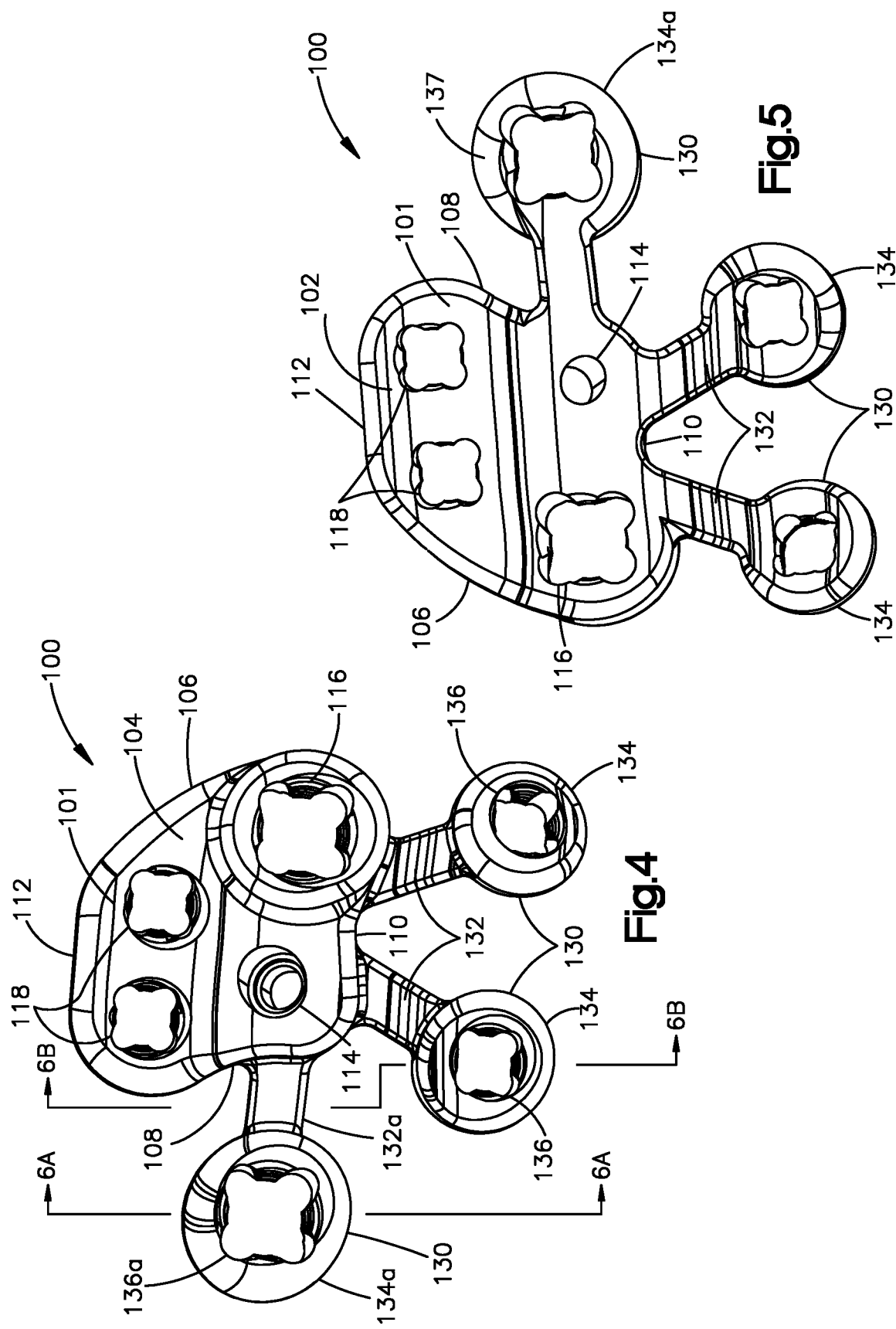

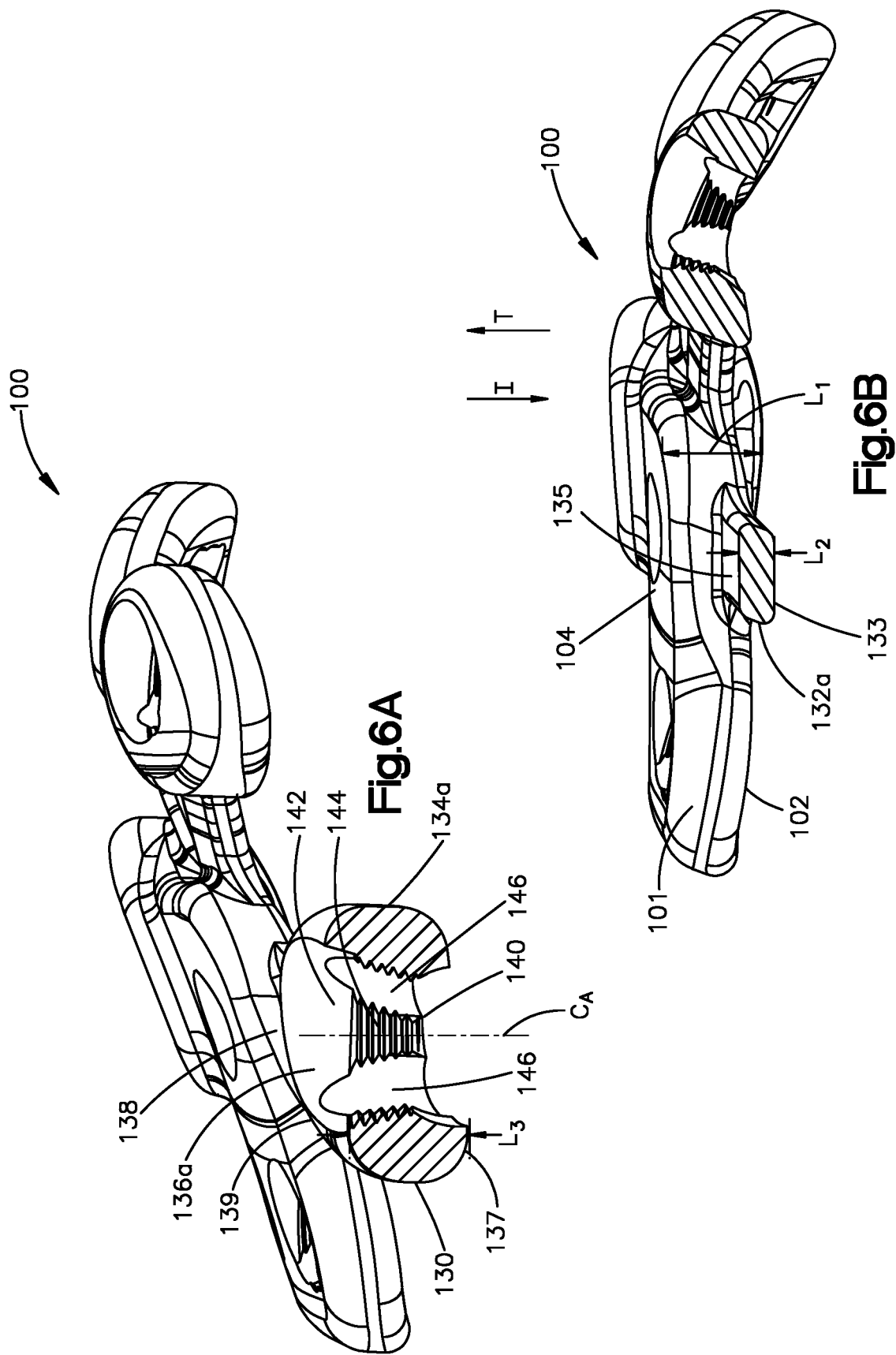

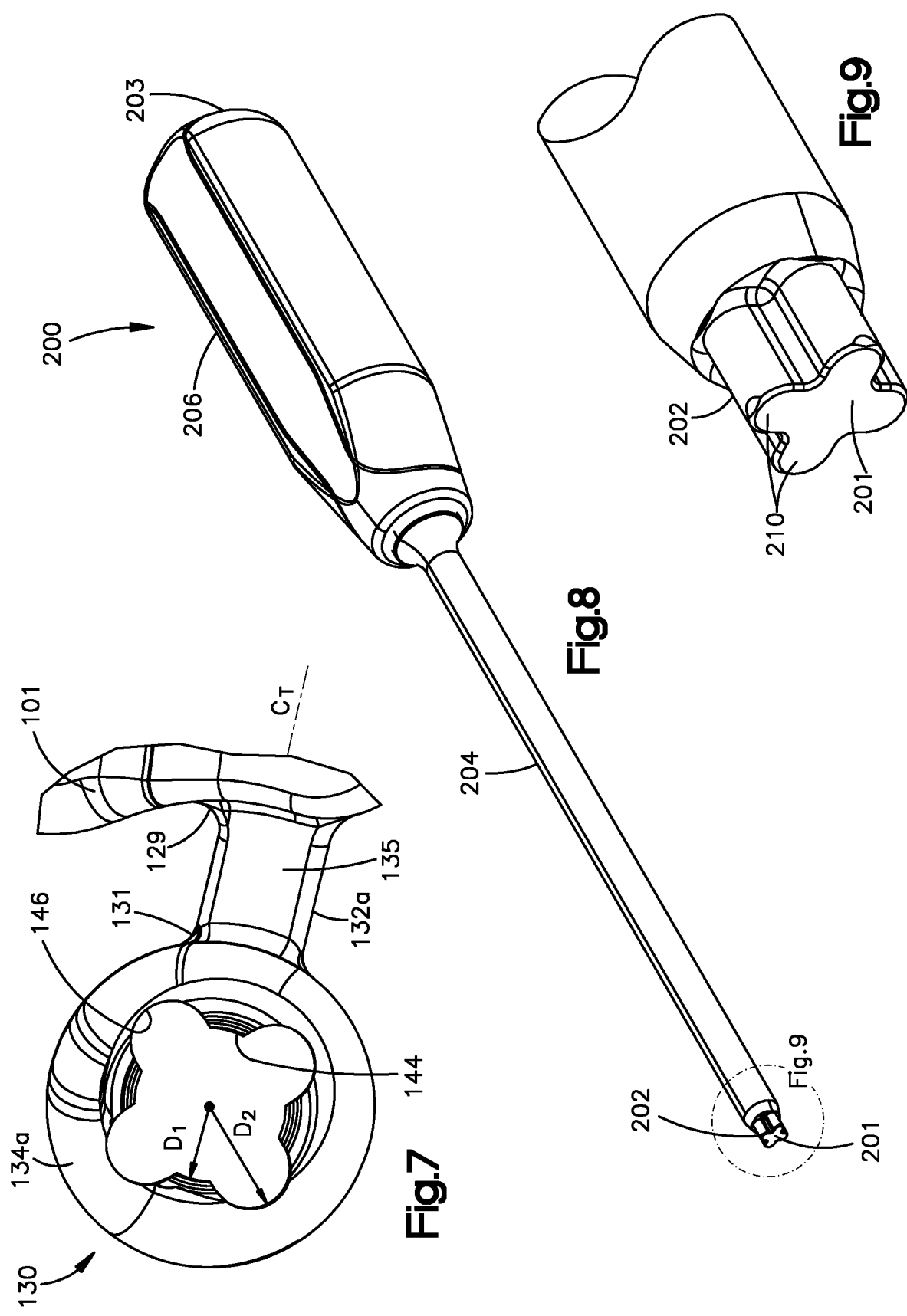

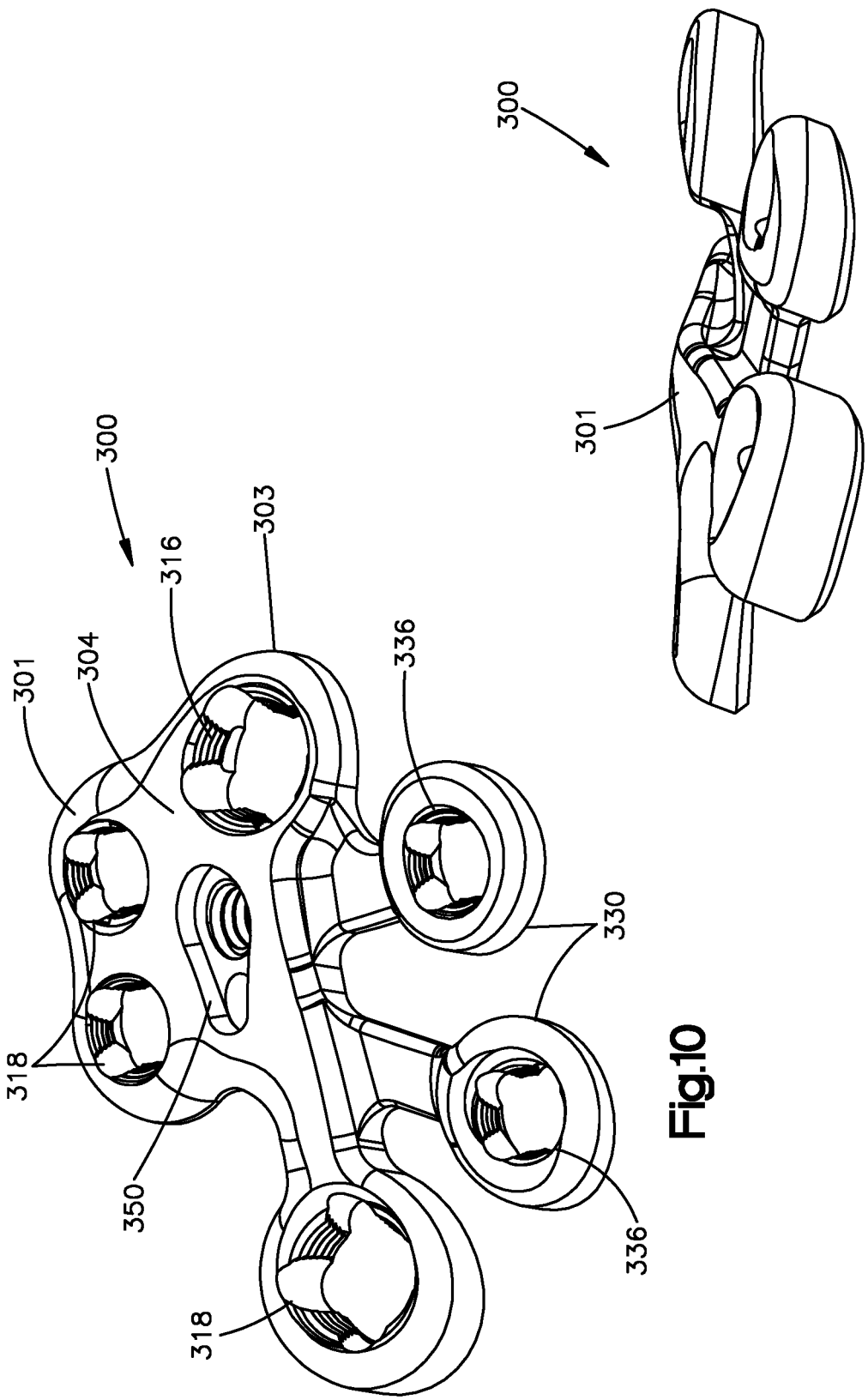

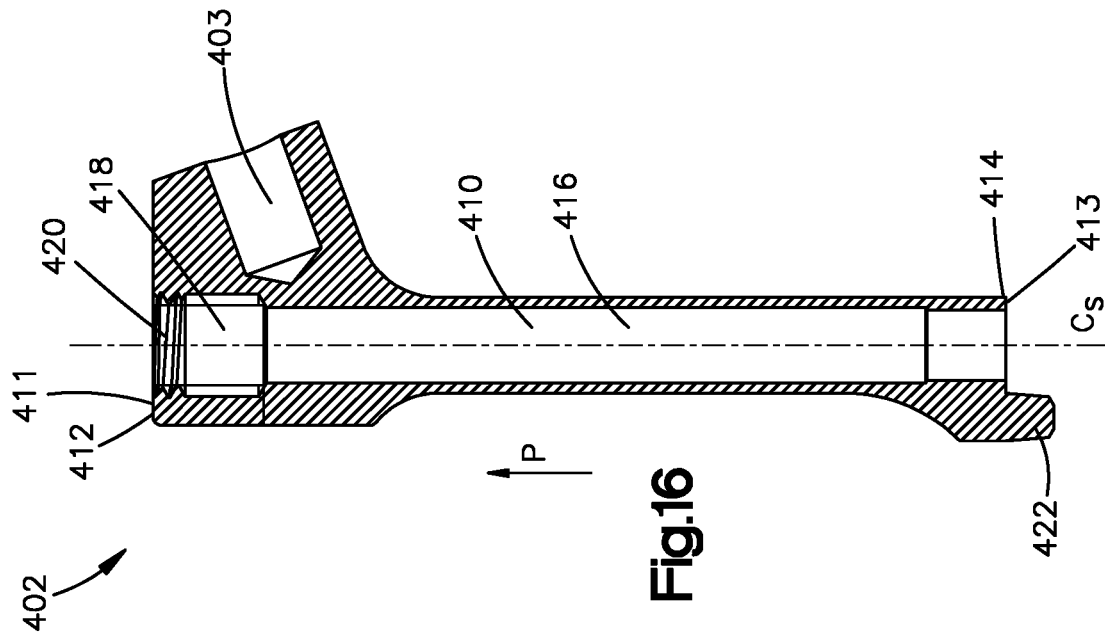
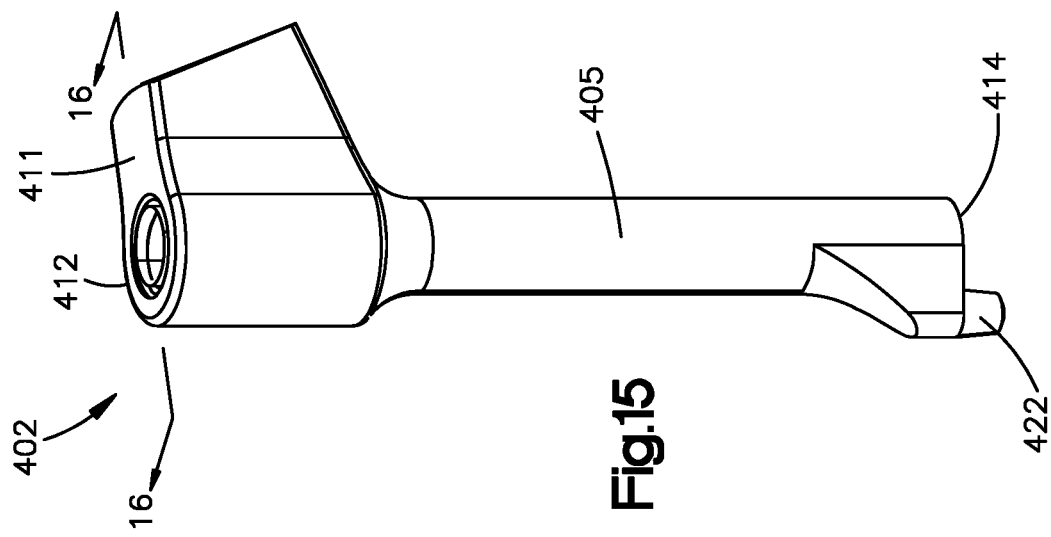

BONE PLATE, BONE PLATE SYSTEM, AND METHOD OF USING THE SAME

TECHNICAL FIELD

The present disclosure relates to systems, kits, assemblies, and methods for the placement and fixation of a bone plate against a bone for attachment to an intramedullary nail in a medullary canal of the bone.

BACKGROUND

Intramedullary nails have long been used to treat fractures in long bones of the body such as fractures in femurs, tibias, and humeri. To treat such fractures, the intramedullary nail is inserted into a medullary canal of the long bone such that the nail extends across one or more fractures in the long bone to segments of the long bone that are separated by the one or more fractures. Bone anchors are then inserted through the bone and into the intramedullary nail on opposing sides of the fracture, thereby fixing the intramedullary nail to the bone. The intramedullary nail can remain in the medullary canal at least until the fracture is fused.

The foregoing background discussion is intended solely to aid the reader. It is not intended to limit the innovations described herein. Thus, the foregoing discussion should not be taken to indicate that any particular element of a prior system is unsuitable for use with the innovations described herein, nor is it intended to indicate that any element is essential in implementing the innovations described herein.

SUMMARY

The foregoing needs are met, to a great extent, by the system and method disclosed in the present application.

Retrograde femoral nailing is often used for fixation of far distal fractures of the femur. When this occurs, often in combination with poor bone quality and/or in periprosthetic settings, additional bone fixation may be required. The proposed system links a small plate or washer to the distal end of the nail by means of a plurality of bone screws. In addition, there will be a plurality of peripheral bone screws that engage more bone than the nail's bone screws alone would, for improved fixation. Proper placement of the washer may present difficulty without the aid of an appropriate holding instrument. Attachment of a holding instrument may present difficulty to operating personnel, and/or the connection may not be rigid enough.

The disclosure relates to a bone plate comprising a plate body and at least one tab. The plate body defines an inner body surface configured to face an underlying bone, an outer body surface opposite the inner body surface, and an outer side surface that extends between the inner body surface and the outer body surface. The outer side surface defines an outer perimeter of the plate body. The at least one tab includes a head and an arm that extends from the plate body to the head. The tab defines a tab aperture that extends through the head and is configured to receive a bone anchor body. The arm is configured to deflect with respect to the plate body so as to move the head between a pre-fixation position and a fixation position spaced from the pre-fixation position.

According to another aspect of the present disclosure, a surgical kit for securing the bone plate to a bone is provided. The surgical kit comprises the bone plate and a bone plate adjustment tool. The bone plate adjustment tool is configured to be received within the tab aperture of the at least one tab member to transition the at least one tab member from the pre-fixation position to the fixation position.

According to another aspect of the present disclosure, a bone plate holder for holding a bone plate during a surgical procedure is disclosed. The bone plate holder comprises a body and a shaft. The body defines a channel that extends through the body from a proximal surface of the body to a distal surface of the body. The shaft has a distal end that includes a coupling element configured to couple the shaft to the bone plate, and the shaft further having a proximal end opposite the distal end, wherein the proximal end includes a control element configured to control the coupling element to couple to the bone plate. The shaft is configured to extend through the channel, such that the coupling element extends out from the distal surface of the body.

This summary is provided to introduce a selection of concepts in a simplified form that are further described below in the Detailed Description section. This Summary is not intended to identify key features or essential features of the claimed subject matter, nor is it intended to be used to limit the scope of the claimed subject matter. Furthermore, the claimed subject matter is not constrained to limitations that solve any or all disadvantages noted in any part of this disclosure.

BRIEF DESCRIPTION OF THE DRAWINGS

The foregoing summary, as well as the following detailed description of illustrative embodiments of the implant of the present application, will be better understood when read in conjunction with the appended drawings. For the purposes of illustrating the implants of the present application, there is shown in the drawings illustrative embodiments. It should be understood, however, that the application is not limited to the precise arrangements and instrumentalities shown. In the drawings:

FIG. 2 illustrates a top perspective view of a bone plate, according to an aspect of this disclosure;

FIG. 3 illustrates a view of a side of the bone plate shown in FIG. 2;

FIG. 4 illustrates a top view of the bone plate shown in FIG. 2;

FIG. 5 illustrates a bottom view of the bone plate shown in FIG. 2;

FIG. 6A illustrates a side cross-section view of the bone plate taken along line 6A-6A in FIG. 4;

FIG. 6B illustrates a side cross-section view of the bone plate taken along line 6B-6B in FIG. 4;

FIG. 7 illustrates a close-up top view of at least one tab member of the bone plate shown in FIG. 2;

FIG. 8 illustrates a perspective view of a bone plate adjustment tool, according to an aspect of this disclosure;

FIG. 9 illustrates a close-up view of a distal end of the bone plate adjustment tool shown in FIG. 8;

FIG. 10 illustrates a top perspective view of another aspect of a bone plate, according to an aspect of this disclosure;

FIG. 11 illustrates a view of a side of the bone plate shown in FIG. 10;

FIG. 15 illustrates a perspective view of a body of the bone plate holder shown in FIG. 14;

FIG. 16 illustrates a cross-sectional view of the bone plate holder shown in FIG. 15 taken along line 16-16;

DETAILED DESCRIPTION OF ILLUSTRATIVE EMBODIMENTS

Figure 1:
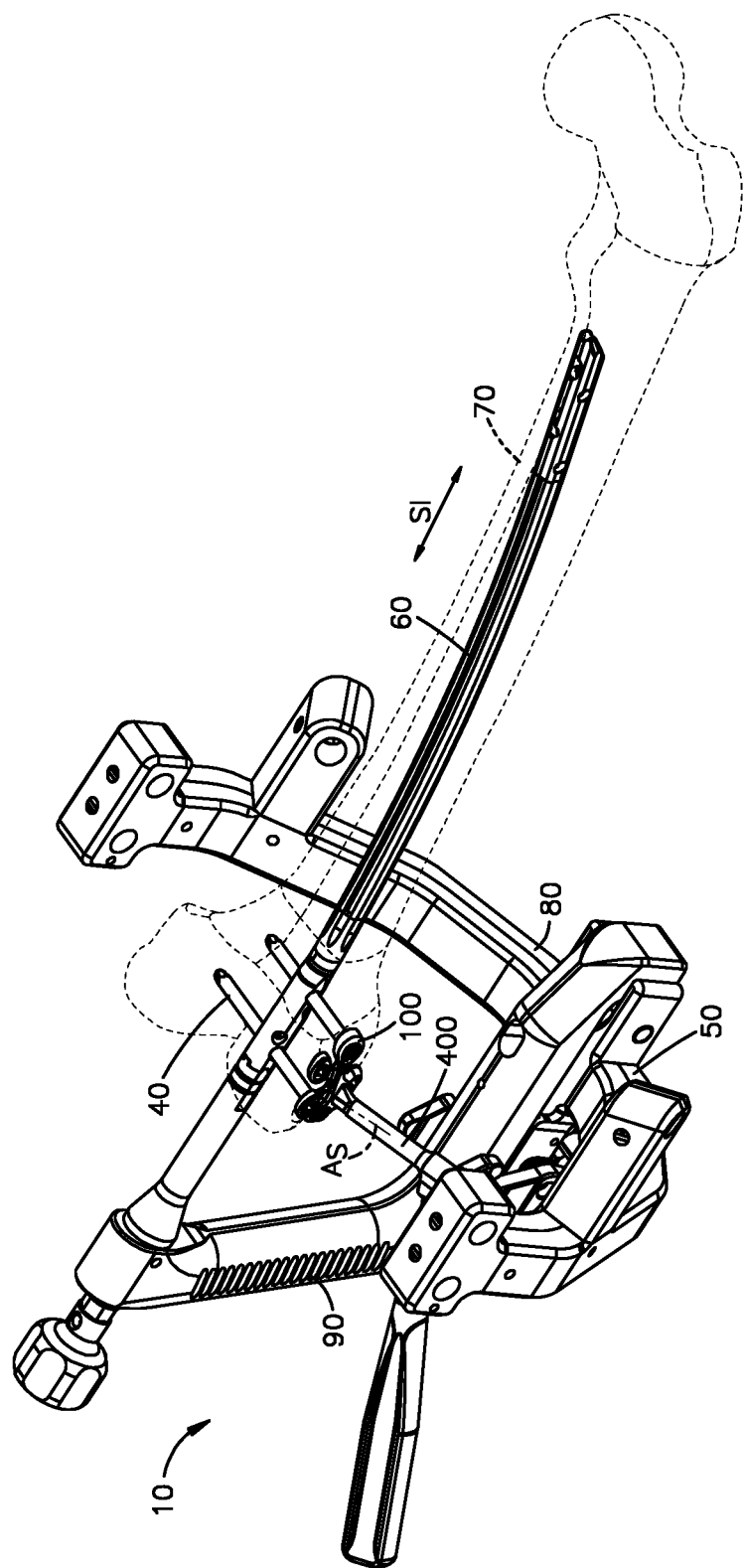
FIG. 1 illustrates a perspective view of a system according to one aspect having a bone plate holder supported and an aiming assembly that is attached to an intramedullary nail received in a medullary canal of a bone.
Figure 12:
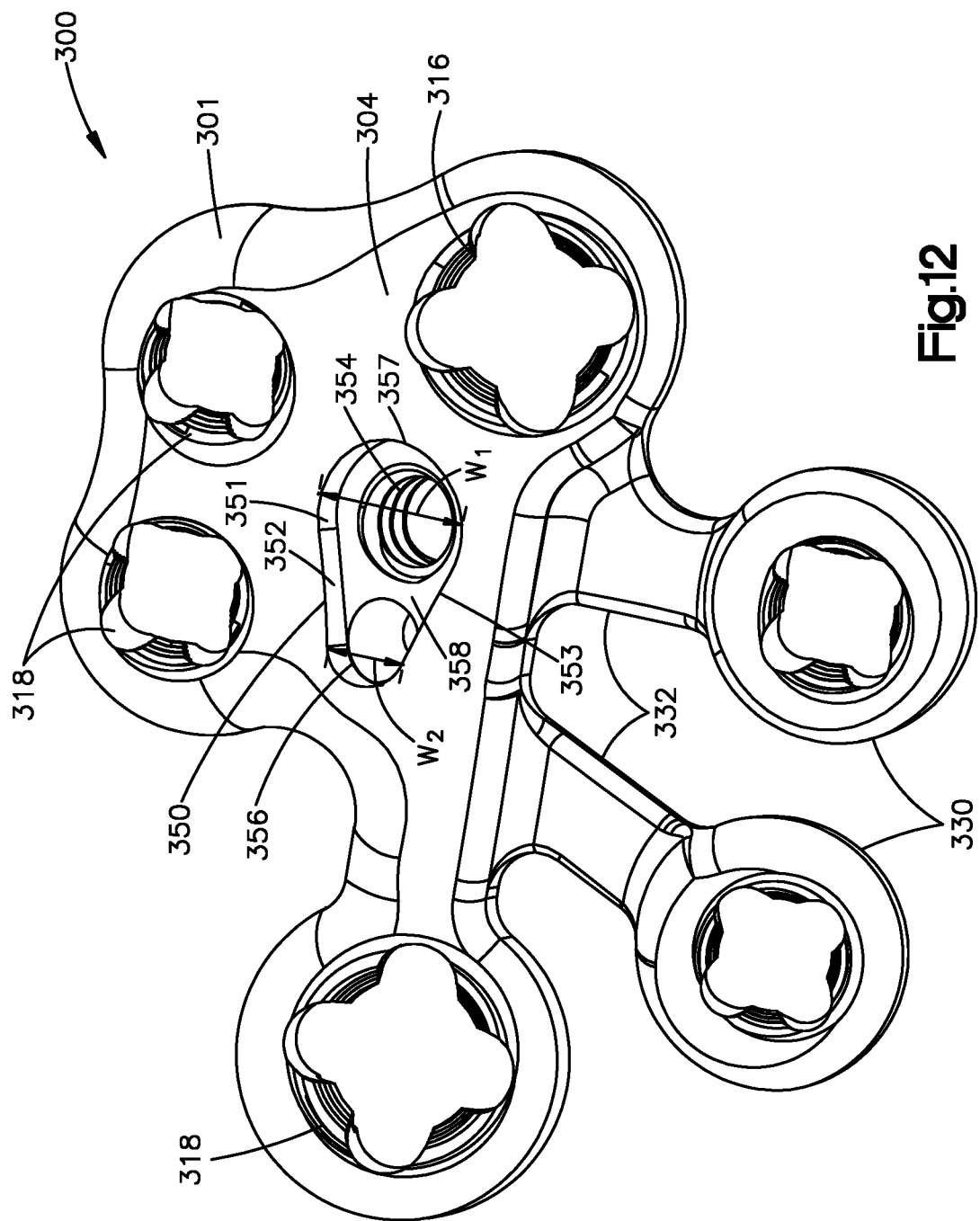
FIG. 12 illustrates a top view of the bone plate shown in FIG. 10.
Figure 13:
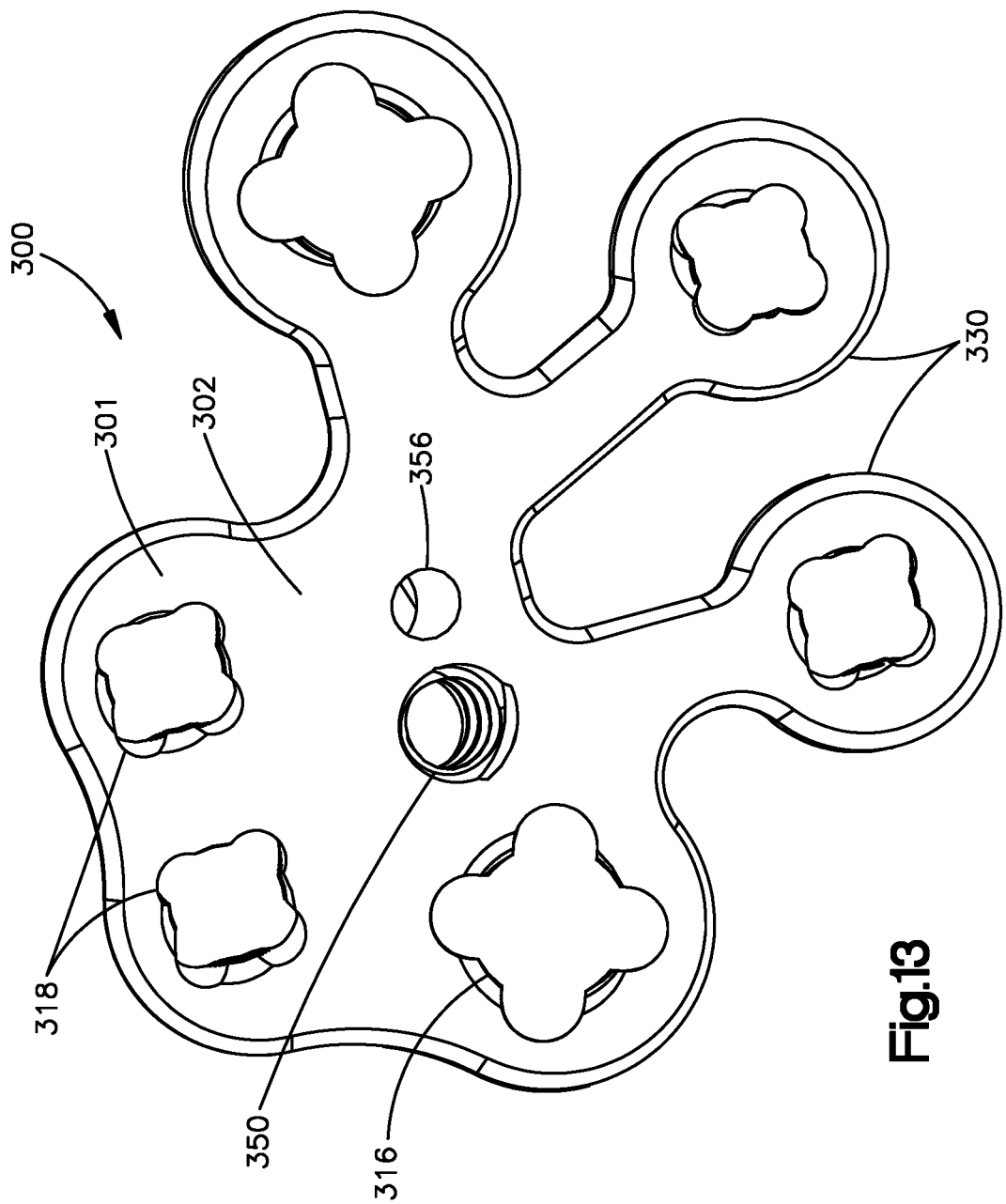
FIG. 13 illustrates a bottom view of the bone plate shown in FIG. 10.
Figure 14:
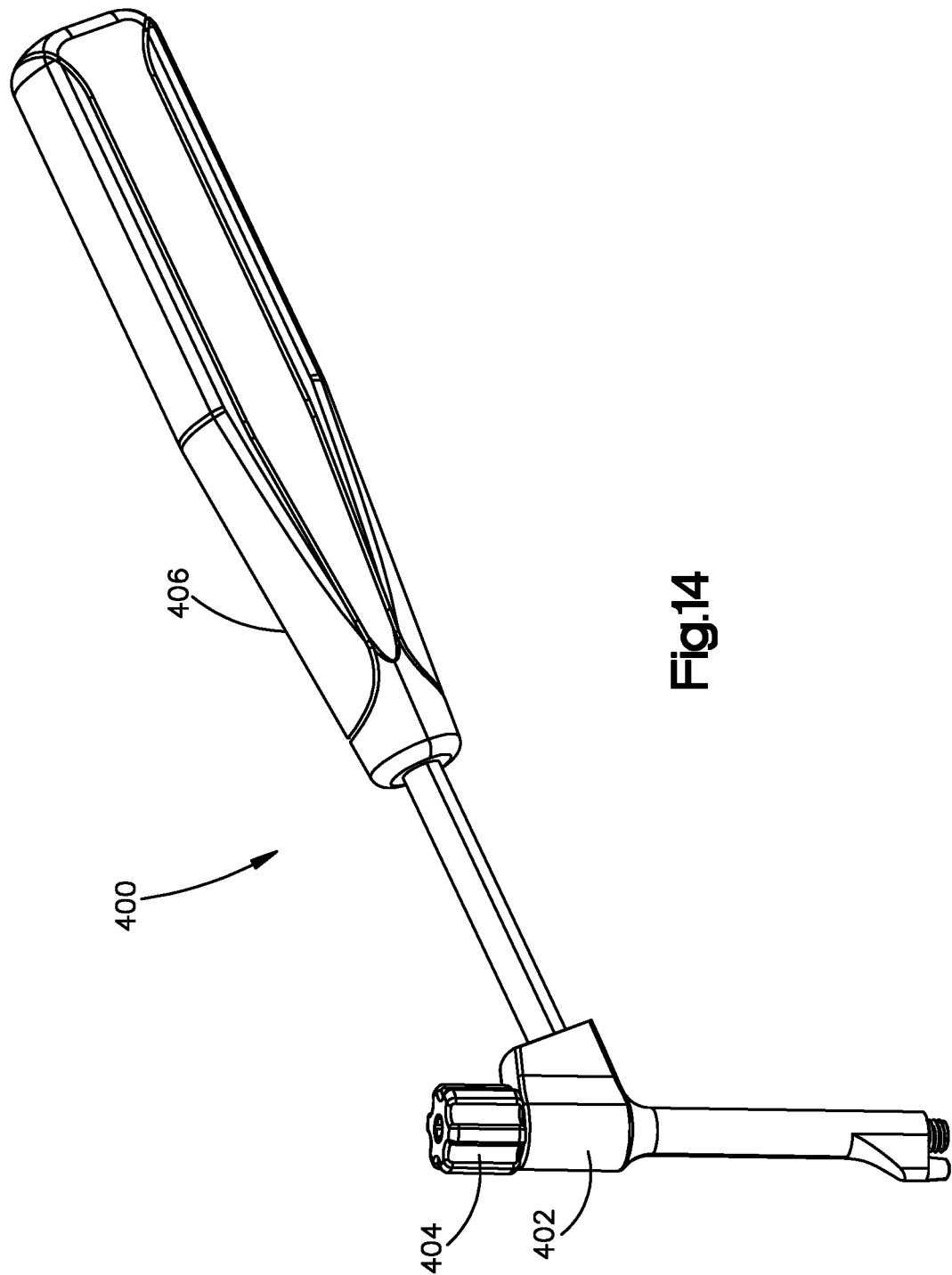
FIG. 14 illustrates a perspective view of a bone plate holder, according to an aspect of this disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

Certain terminology used in this description is for convenience only and is not limiting. The words "top", "bottom", "distal", "proximal", "inward", "outward", "inner", "outer", "above", "below", "axial", "transverse", "circumferential," and "radial" designate directions in the drawings to which reference is made. The words "inner", "internal", and "interior" refer to directions towards the geometric center of the implant and/or implant adjustment tools, while the words "outer", "external", and "exterior" refer to directions away from the geometric center of the implant and/or implant adjustment tools. The words, "anterior", "posterior", "superior," "inferior," "medial," "lateral," and related words and/or phrases are used to designate various positions and orientations in the human body to which reference is made. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. The terminology includes the above-listed words, derivatives thereof and words of similar import.

As used herein, the term "substantially" and derivatives thereof, and words of similar import, when used to describe a size, shape, orientation, distance, spatial relationship, or other parameter includes the stated size, shape, orientation, distance, spatial relationship, or other parameter, and can also include a range up to 10% more and up to 10% less than the stated parameter, including 5% more and 5% less, including 3% more and 3% less, including 1% more and 1% less.

An intramedullary nail is commonly secured to bone via at least one bone anchor, where each bone anchor extends directly into the surface of the bone and into a corresponding bone-anchor aperture in the intramedullary nail such that the bone anchor attaches to both the bone and the nail. However, as forces are exerted on the intramedullary nail, the attachment or bond between the bone anchor and the bone can weaken. This is especially true for patients whose bone at the bone anchor site is weakened due to osteoporosis or other bone conditions. To strengthen the attachment between the bone anchor and the bone, the bone anchor can be further secured to a bone plate that is positioned against the outer surface of the bone and secured to the bone via one or more additional bone anchors. For example, the bone plate can be positioned against the bone, and a first bone anchor can be inserted into an aperture in the plate, through the surface of the bone, and into the intramedullary nail, such that the first bone anchor attaches to the plate, the bone, and the intramedullary nail. Further, one or more other bone anchors can be inserted into the plate adjacent the first bone anchor such that the one or more other bone anchors terminate in the bone with or without passing into the intramedullary nail. The one or more other bone anchors provide additional fixation to the bone that can reduce loading on the first bone anchor.

Referring to FIG. 1, a system 10 is shown that is configured to position a bone plate 100 against a surface of a bone 70 as the bone plate 100 is fastened to the bone 70 and an intramedullary nail 60. In general, the system 10 comprises a bone plate holder 400 (e.g. a bone-plate placement tool) that supports the bone plate 100 and angulates the bone plate 100 so as to align a surface of the bone plate 100 with a surface of the bone 70. The system further comprises a bone plate adjustment tool 200 (see FIG. 8) to facilitate fixation of the bone plate 100 to the bone 70.

The system 10 can further comprise one or more of the bone plates 100, at least one bone anchor 40 such as a bone screw, an aiming assembly 50, and an intramedullary nail 60. The intramedullary nail 60 is elongate generally along a superior-inferior direction SI and is sized to be received in a medullary canal of a long bone such as a femur, tibia, or humerus. The aiming assembly 50 releasably attaches to a proximal end of the intramedullary nail 60 and can comprise an aiming guide 80 and a handle 90. The aiming assembly 50 can facilitate alignment of the bone plate 100 such that an axis $A_S$ of the bone plate 100 is aligned with the bone plate holder 400 and the intramedullary nail 60. For example, the axis of the bone plate 100 can be aligned with a bone-anchor opening that extends through the intramedullary nail 60.

Referring to FIGS. 2-7, the bone plate 100 includes a plate body 101 having an inner body surface 102 (e.g. a bone-facing surface) and an outer body surface 104 opposite the bone-facing surface 102 along a transverse direction T. The body-facing surface 102 can have a curved shape, contoured shape, or other shape configured to align with the surface of the bone 70. The bone plate 100 includes an outer side surface 103 that extends about an outer perimeter of the plate body 101. The outer side surface 103 can have a first transverse side 106 and a second transverse side 108 opposite from one another. The first and second transverse sides 106 and 108 can extend from the bone-facing surface 102 to the outer body surface 104. The outer side surface 103 can additionally or alternatively have a first lateral side 110 and a second lateral side 112 opposite from one another. The first and second lateral sides 110 and 112 can extend from the bone-facing surface 102 to the outer body surface 104. The first and second lateral sides 110 and 112 can extend from the first transverse side 106 to the second transverse side 108. It will be understood that embodiments of the disclosure are not limited to the specific bone plate shown in FIGS. 2-7, and that alternative bone plates are contemplated (e.g. see bone plate 300 in FIGS. 10-13).

The bone plate 100 defines a first bone-anchor aperture 116 configured to be aligned with a shaft longitudinal axis $A_{S1}$ (see FIG. 23) when the bone plate 100 is fastened to the bone-plate placement tool 400. Thus, the longitudinal axis $A_{S1}$ can extend through the first bone-anchor aperture 116 when the bone plate 100 is fastened to the bone plate holder 400. Further, the bone plate holder 400 is configured to align the longitudinal axis $A_{S1}$ with the first bone-anchor aperture 116 over a full range of angles of the holder 400, without impeding with a path of a bone anchor or drill bit with the bone plate holder 400. The first bone-anchor aperture 116 can extend through the bone plate 100 from the outer body surface 104 to the bone-facing surface 102 so as to receive a bone anchor 40 (FIG. 1) to attach the bone plate 100 to the bone 70. The first bone-anchor aperture 116 can be threaded to receive a threaded head of a bone anchor. Further, the first bone-anchor aperture 116 can define variable-angle threading that permits a bone anchor to be inserted into the first bone-anchor aperture 116 at varying angles. Alternatively, the bone-anchor aperture 116 can be unthreaded.

The bone plate 100 defines at least one additional bone-anchor aperture 118, such as a plurality of additional bone-anchor apertures 118. The at least one additional bone-anchor aperture 118 is spaced from the first bone-anchor aperture 116 such that the at least one additional bone-anchor aperture 118 is offset from (i.e., not aligned with) the shaft longitudinal axis $A_{S1}$ when the bone plate 100 is fastened to the bone-plate placement tool 20. The at least one additional bone-anchor aperture 118 extends through the bone plate 100 from the outer body surface 104 to the bone-facing surface 102. At least one of the bone-anchor apertures 118 can be threaded to receive a threaded head of a bone anchor. Further, each bone-anchor aperture 118 can define variable-angle threading that permits a bone anchor to be inserted into the bone-anchor aperture 118 at varying angles. Alternatively, each additional bone-anchor aperture 118 can be unthreaded.

The bone plate 100 defines at least one, such as a plurality of, bone-plate fasteners 114 configured to engage a fastener of the bone plate holder 400 so as to fasten the bone plate 100 to the holder 400. Each of the at least one bone-plate fasteners 114 can define an aperture configured to receive a corresponding fastener of the holder 400 so as to fasten the bone plate 100 to the holder 400. For example, each fastener 114 can be configured to receive a projection that extends from the bone-plate placement tool 20. It will be understood that any other suitable fasteners can be used to releasably fasten the bone plate 100 to the bone plate holder 400. For example, the fastener 114 can comprise a fixation element 350, as further described below.

The bone plate 100 further includes at least one tab member 130. The at least one tab member 130 extends from the outer side surface 103 of the bone plate 100. For example, the at least one tab 130 can extend from any one the first and second transverse sides 106 and 108 and the first and second lateral sides 110 and 112, and/or can extend from multiple sides 106, 108, 110, and 112 of the bone plate 100. For example, FIGS. 2, 4, and 5 illustrate two tabs 130 that extend from the first lateral side 110, and a single tab 130 that extends from the second transverse side 108. Each of the at least one tabs 130 can extend in an outward direction (e.g. radial direction) from the outer side surface 103 of the bone plate 100. In an aspect, each of the at least one tabs 130 extend in a direction from the outer side surface in a direction that is offset from the shaft longitudinal axis $A_{S1}$ when the bone plate 100 is fastened to the bone-plate placement tool 20. Each of the at least one tabs 130 can extend substantially parallel to each of the other tabs 130, can be angularly offset from each of the other tabs 130, or combinations of offset and parallel (e.g. some tabs 130 are parallel to each other, while other tabs 130 are angularly offset from other tabs 130).

Each tab 130 comprises an arm 132 and a head 134. The arm 132 extends between the plate body 101 of the bone plate 100 and the head 134. The arm 132 and the head 134 can be integrally formed as a single unitary piece. In an aspect, each tab 130 and the body 101 of the bone plate 100 can be integrally formed as a single unitary piece. Alternatively, at least one of the tabs 130 can be coupled to (e.g. attachable) to the body 101 of the bone plate 100.

Each arm 132 can extend in an outward direction from the outer side surface 103 of the plate body 101. Each arm 132 can extend substantially perpendicular to the outer side surface 103. Alternatively, each arm 132 can extend at an angle other than substantially perpendicular to the outer side surface 103. For example, with reference to FIG. 4, each arm 132 that extends from the first lateral side 110 extends in the outward direction at an angle of between 0 and 90 degrees. The arm 132a that extends from the second transverse side 108 extends in the outward direction at an angle of approximately 90 degrees. Each arm 132 can also extend in an inward or outward direction from the plate body 101. For example, with reference to FIG. 4, the arm 132a that extends from the second transverse side 108 extends at least partially in an inward direction. The position and angle of each of the tabs 130 extending from the plate body 101 can depend on, for example, the anatomy of the patient, the size and/or shape of the intramedullary nail 60, the location of corresponding apertures in the intramedullary nail 60, or other factors.

The head 134 of each tab 130 can define a tab aperture 136 that extends therethrough. With reference to FIGS. 6A and 7, the tab aperture 136a extends through the head 134 from an upper opening 138 to a lower opening 140. Each of the upper and lower openings 138 and 140 can be substantially perpendicular to a central aperture axis $C_A$. The central aperture axis $C_A$ extends through a center of the tab aperture 136a. Alternatively, the upper and lower openings 138 and 140 can be angularly offset from a direction that is substantially perpendicular to the central aperture axis $C_A$. For example, the lower opening 140 can be offset from the direction substantially perpendicular to the central aperture axis $C_A$ to align with an anatomy of the patient.

The bone-anchor aperture 136a further includes an inner surface 142 that extends about the central aperture axis $C_A$.

The inner surface 142 can define at least one column 144. The at least one column 144 can extend about the central aperture axis $C_A$ from the upper opening 138 to the lower opening 140. Alternatively, the at least one column 144 may extend about a portion of the inner surface 142. For example, the at least one column 144 can extend from the lower opening 140 to a location between the upper and lower openings 138 and 140. The at least one column 144 can include threads. In an aspect, the threads of the at least one column 144 can define variable-angle threading that permits a bone anchor to be inserted into the bone-anchor aperture 136a at varying angles. Alternatively, the at least one column 144 of the bone-anchor aperture 136a can be unthreaded.

The inner surface 142 can further define a receiving element 146. The receiving element 146 is configured to receive the bone plate adjustment tool 200, as further described below. The inner surface 142 can define a first cross-sectional dimension $D_1$ (e.g. radial dimension extending from central aperture axis $C_A$), and the receiving element 146 can define a second cross-sectional dimension $D_2$ (e.g. radial dimension extending from central aperture axis $C_A$) that is greater than the first cross-sectional dimension $D_1$. The receiving element 146 can comprise one or more recesses that include curved, lobed, rectangular, and/or other shapes. For example, the receiving element 146 can include a single or multi-lobe configuration, whereby each lobe of the receiving element 146 is spaced radially outward from the first cross-sectional dimension $D_1$ of the inner surface 142 relative to the central aperture axis $C_A$. The number and spacing of the lobes of the receiving element 146 can correspond to a number and spacing of a connection element 202 of the bone plate adjustment tool 200.

The receiving element 146 can extend through the bone-anchor aperture 136a from the upper opening 138 to the lower opening 140. Alternatively, the receiving element 146 can extend partially through the bone-anchor aperture 136a from the upper opening 138 to a location on the inner surface 142 between the upper and lower openings 138 and 140. The receiving element 146 is configured to receive the bone plate adjustment tool 200 through the upper opening 138 and into the bone-anchor aperture 136a.

The receiving element 146 can be spaced circumferentially about the inner surface 142. For example, if the receiving element 146 includes 4 lobes, each lobe can be spaced approximately 90 degrees apart from each of the other lobes (e.g. cloverleaf configuration). Alternatively, each lobe of the receiving element 146 can be spaced at varying degrees about the inner surface, so long as the lobes correspond to the connection element 202 of the bone plate adjustment tool 200. The receiving element 146 can also circumferentially intersect with the at least one column 144 defined by the inner surface 142, forming peripheral areas of thread relief arranged about the inner surface 142. For example, for a receiving element 146 including 4 lobes spaced 90 degrees apart, the at least one column 144 can be positioned within the circumferential length of the 90 degrees between each lobe. In this example, the at least one column 144 can include 4 sections spaced circumferentially about the inner surface 142 configured to receive and engage a bone-anchor positioned within the bone-anchor aperture 136a. If the at least one column 144 includes a threaded section, the threaded section can threadedly engage a corresponding threaded section of a bone-anchor.

Each of the bone-anchor apertures 136 defined by each tab 130 can be configured substantially similarly as each of the other bone-anchor apertures 136. For example, the bone-anchor apertures 136 defined by the tabs 130 extending from the first lateral side 110 of the plate body 101 can have the same dimensions, threaded sections, receiving elements, or other features as the bone-anchor aperture 136a defined by the tab 130 extending from the second transverse side 108 of the plate body 101. Alternatively, each of the bone-anchor apertures 136 can be configured differently from one or more of the other bone-anchor apertures 136. For example, a cross sectional dimension (e.g. diameter and/or circumference) of the bone-anchor aperture 136a defined by the tab 130 extending from the second transverse side 108 of the plate body 101 can be greater than a cross sectional dimension of one or more of the tab apertures 136 defined by the tabs 130 extending from the first lateral side 110 of the plate body 101 and/or any of the other sides 106 and 112 of the plate body 101. The particular configuration of the bone-anchor aperture 136 can correspond to the particular bone anchor being received within the aperture 136.

The at least one additional bone-anchor aperture 118 and the first bone-anchor aperture 116 can be configured in a substantially similar manner as the tab apertures 136 defined by the tabs 130. For example, at least one or more of the additional bone-anchor apertures 118 and the first bone-anchor aperture 116 can include the receiving element 146 and the at least one column 144. Each receiving element 146 of the bone-anchor apertures 116 and 118 can be configured to correspond to the connection element 202 of the bone plate adjustment tool 200.

Each of the tabs 130 can be configured to flex and/or bend between multiple positions. Each of the tabs 130 can transition between a pre-fixation position, in which the head 134a is in a first position, and a fixation position, in which the head 134a is in a second position spaced from the first position. The flexing of the tabs 130 is discussed further below with reference to FIG. 24. The tabs 130 can comprise a grade of stainless steel or other material adapted to plastically deform. In an aspect, the tabs 130 can comprise a carburized stainless steel to avoid galvanic corrosion caused between the contact between the tab 130 and the bone-anchor 40 positioned within the bone-anchor aperture 136. For example, the intramedullary nail 60 can comprise titanium or a titanium alloy due to its low elastic modulus that encourages bone healing. If the bone-anchor 40 is made from either a stainless steel or a titanium, there can be a risk of galvanic corrosion on one end of the anchor 40 or another, where disparate metals contact each other. In an alternative aspect, the bone-anchor 40 can comprise a carburized stainless steel to avoid galvanic corrosion. It will be appreciated that other materials can be used to form the tabs 130, the plate body 101, and the anchors 40, including, for example, cobalt chrome, cobalt chrome alloys, or still other materials.

The arms 132 of each of the tabs 130 can include a substantially flat configuration. For example, each arm 132 can have a width that is greater than a thickness of the arm 132. The flat configuration can facilitate bending, and in particular, can facilitate bending in a desired direction. For example, the arm 132 can bend in directions substantially perpendicular to the width of the arm 132. The arm 132 can be aligned with respect to the plate body 101 of the bone plate 100 such that the arm 132 can be bent to substantially align a contour of the bottom surface of the tab 130 with a contour of the surface of the bone 70 of the patient during a surgical procedure.

Referring to FIG. 6B, the outer body surface 104 is spaced from the inner body surface 102 a first distance $L_1$ along the transverse direction T so as to define a plate body 101 thickness. The arm 132a defines an inner arm surface 133 configured to face the underlying bone 70. The arm 132a further defines an outer arm surface 135 opposite the inner arm surface 133 along the transverse direction T. The outer arm surface 135 is spaced from the inner arm surface 133 by a second distance $L_2$ in the transverse direction T so as to define an arm 132a thickness. The first distance $L_1$ that defines the plate body 101 thickness can be greater than the second distance $L_2$ that defines the arm 132a thickness.

The inner arm surface 133 is spaced from the outer arm surface 135 in an inward direction I that is oriented along the transverse direction T. In an aspect, the outer arm surface 135 is offset from the outer body surface 104 in the inward direction I. In an alternative or additional aspect, the outer arm surface 135 is offset with respect to the outer head surface 139 in the inward direction I. The inner arm surface 133 can be continuous with the inner head surface 137. For example, the inner arm surface 133 may not be offset from the inner head surface 137 in the inward direction I such that the inner arm surface 133 extends adjacent to the inner head surface 137 without interruption. Alternatively, the inner arm surface 133 can be offset from the inner head surface 137 in the inward direction I.

Referring to FIG. 7, the arms 132a can extend from the plate body 101 to the head 134 along a central tab axis CT. Each arm 132a can be configured to twist about the central axis CT so as to move the head 134 from the pre-fixation position to the fixation position. Each arm 132 can include a first taper portion 129 and a second taper portion 131. The first taper section 129 is located adjacent to the body 101. The outer arm surface 135 within the first taper section 129 can taper in an outward direction. The outward direction being opposite the inward direction I. The inner arm surface 133 within the first taper section 129 can taper in the inward direction I. For example, the thickness of the arm 132a within the first taper section 129 can be greater than a thickness of the arm 132 along a length of the arm between the first taper section 129 and the second taper section 131.

The second taper section 131 is located adjacent to the head 134a. The outer arm surface 135 within the second taper section 131 can taper in an outward direction. The inner arm surface 133 within the second taper section 131 can taper in the inward direction I. For example, the thickness of the arm 132a within the second taper section 131 can be greater than a thickness of the arm 132a along a length of the arm between the first taper section 129 and the second taper section 131.

Alternatively, or additionally, a width of the arm 132a within the first taper section 129 and the second taper section 131 can increase along its length from the arm 132a toward the body 101 and along its length from the arm 132a toward the head 134a, respectively. The width of the arm 132a defining a dimension that is substantially perpendicular to the inward direction I and the length of the arm 132a between the first and second taper sections 129 and 131. The width of the arm 132a within the first taper section 129 can be greater than a width of the arm 132a along its length between the first and second taper sections 129 and 131, and a width of the arm 132a within the second taper section 131 can be greater than a width of the arm 132a along its length between the first and second taper sections 129 and 131.

The head 134a defines an inner head surface 137 configured to face the underlying bone, and an outer head surface 139 opposite the inner head surface 137. The outer head surface 139 is spaced from the inner head surface 137 by a third distance $L_3$ so as to define a head 134a thickness. In an aspect, the third distance $L_3$ defining the head 134a thickness is substantially equal to the first distance $L_1$ defining the plate body 101 thickness. In another aspect, the third distance $L_3$ defining the head 134a thickness is substantially equal to the second distance $L_2$ that defines the arm 132a thickness. In an aspect, the thicknesses of the arm 132a, the head 134a, and the plate body 101 can be different.

Referring to FIGS. 8 and 9, the bone plate adjustment tool 200 includes the connection element 202, a shaft 204, and a handle 206. The connection element 202 is positioned at the distal end 201 of the adjustment tool 200. The shaft 204 extends between the connection element 202 and the handle 206. In an aspect, the connection element 202 extends distally from a distal most end of the shaft 204. The handle 206 extends from the shaft 204 toward a proximal end 203 of the adjustment tool 200. The handle 206, the shaft 204, and the connection element 202 can be rigidly connected together such that movement and/or rotation of the handle 206 causes movement and/or rotation of the connection element 202. The bone plate adjustment tool 200 is configured to engage and transition the tabs 130 from the pre-fixation position to the fixation position.

The connection element 202 can comprise one or more protrusions 210 that include curved, lobed, rectangular, and/or other shapes. For example, the connection element 202 can include a single or multi-lobe configuration, whereby each lobe (e.g. protrusion 210) of the connection element 202 protrudes in a radially outward direction. Each lobe of a multi-lobe configuration can be spaced circumferentially about a center of the connection element 202. The number and spacing of the protrusions 210 of the connection element 202 can correspond to a number and spacing of recesses of the receiving element 146 defined by the bone plate 100.

The connection element 202 is configured to engage the receiving element 146 to at least temporarily connect the adjustment tool 200 to the bone plate 100. The connection between the adjustment tool 200 and the bone plate 100 can enable the adjustment tool to move and/or manipulate the bone plate 100. For example, the adjustment tool 200 can bend and/or flex the tabs 130. Additionally, the configurations of the receiving element 146 and the connection element 202 can reduce the risk of damage to the inner surface 142 of the bone-anchor aperture 136. For example, if the inner surface 142 includes the at least one column 144 having a threaded region, the configurations of the receiving element 146 and the connection element 202 can reduce the risk of thread damage.

It will be appreciated that more than one bone plate adjustment tools 200 can connect with the bone plate 100. For example, a bone plate 100 having more than one receiving element 146 that have different configurations (e.g. size, shape, etc.), multiple bone plate adjustment tools 200 can be used. In another example, a first bone plate adjustment tool 200 can engage a first bone-anchor aperture 136a, and a second bone plate adjustment tool 200 can engage a second bone-anchor aperture 136a. The first bone plate adjustment tool 200 can used to, for example, transition the tab 130 while the second bone plate adjustment tool 200 provides, for example, a counter torque to maintain the position of the bone plate 100. Each bone plate adjustment tool 200 can comprise a a connection element 202 having a configuration (e.g. size, shape, etc.) that corresponds to a configuration of the respective receiving element 146.

FIGS. 10-13 illustrate an alternate aspect of a bone plate 300, according to aspects of this disclosure. Portions of the alternate aspect of the bone plate 300 disclosed in FIGS. 10-13 are similar to aspects of the bone plate 100 described above in FIGS. 2-7 and those portions function similarly to those described above. The bone plate 300 includes a body 301 having a bone-facing surface 302 and an outer surface 304 opposite the bone-facing surface 302. The bone plate 300 includes an outer side surface 303 that extends about an outer perimeter of the body 301.

The bone plate 300 defines a first bone-anchor aperture 316 that extends through the bone plate 300 from the outer surface 304 to the bone-facing surface 302 so as to receive the bone anchor 40 to attach the bone plate 300 to the bone 70. The bone plate 300 defines at least one additional bone-anchor aperture 318, such as a plurality of additional bone-anchor apertures 318. The at least one additional bone-anchor aperture 318 is spaced from the first bone-anchor aperture 316. The bone plate 300 further includes at least one tab member 330.

The bone plate 300 further includes the fixation element 350. The fixation element 350 extends at least partially through the outer surface 304 and includes a recessed portion 352, a first aperture 354, and a second aperture 356 (e.g. a plate fixation element). The fixation element 350 is configured to receive a bone plate holder 400 within to connect the bone plate 300 to the bone plate holder 400. The fixation element 350 can include fewer or more apertures 354 and 356 to align with corresponding elements of the bone plate holder 400.

The recessed portion 352 extends into the body 301 from the outer surface 304 to an inner recessed surface 358. The first and second apertures 354 and 356 both extend from the inner recessed surface 358 into the body 301 toward the bone-facing surface 302. In an aspect, one or both of the first and second apertures 354 and 356 extend through the body 301 to the bone-facing surface 302. The first aperture 354 can be threaded to receive a corresponding threaded portion of a plate coupling element 432 of the bone plate holder 400. The threads defined by the first aperture 354 can extend along an entire length of the first aperture 354. Alternatively, the threads can extend along a partial length of the first aperture 354. For example, the threads can extend from the inner recessed surface 358 toward the bone-facing surface 302.

The second aperture 356 is spaced apart from the first aperture 354 within the recessed portion 352. The second aperture 356 can be unthreaded and configured to receive a corresponding portion (e.g. a holder fixation element 422) of the bone plate holder 400. The second aperture 356 can have a cylindrical shape, a conical shape, or other shape that corresponds to the holder fixation element 422 of the bone plate holder 400.

In an alternative aspect, one or both of the apertures 354 and 356 can be positioned within the recessed portion 352. For example, one or both of the apertures 354 and 356 can extend into the body 301 from the outer surface 304 toward the bone-facing surface 302.

The recessed portion 352 includes an inner edge 353 extending about a perimeter of the recessed portion 352. The inner edge 353 has a first end 355 spaced from a second end 357 in a plate lateral direction L. The second aperture 356 is positioned between the first aperture 354 and the first end 355 in the plate lateral direction L. The first aperture 354 is positioned between the second end 357 and the second aperture 356 in the lateral direction L. The inner edge 353 tapers in width, as measured in a direction substantially perpendicular to the plate lateral direction L, from a maximum width $W_1$ of the inner edge 353 located toward the second end 357 to a minimum width $W_2$ located toward the first end 355. A length between the maximum width $W_1$ and the minimum width $W_2$ along the inner edge 353 can be substantially linear.

It will be appreciated that the fixation element 350 can include additional elements, for example, additional apertures, retentions elements, recesses/protrusions, or other elements. The fixation element 350 can also include other fixation configurations to connect to the bone plate holder 400. For example, the fixation element 350 can include a snap-fit, friction-fit, or other type of fixation configuration.

FIGS. 14-20 illustrate the bone plate holder 400, according to aspects of this disclosure. The bone plate holder 400 includes a body 402 (e.g. holder body), a shaft 404, and a grip member 406. The grip member 406 is configured to be gripped by a surgeon performing a surgical procedure to align the bone plate holder 400 with the bone plate 100, and to control the position of the bone plate 100 while the bone plate 100 is being fastened to the intramedullary nail 60. The grip member 406 can connect to a handle connection portion 403 of the body 402. The body 402 and the shaft 404 are configured to control connecting and disconnecting the bone plate holder 400 with the bone plate 100.

With reference to FIGS. 15 and 16, the body 402 has an inner surface 410 that extends through the body 402 from a proximal surface 411 at a proximal end 412 of the body 402 to a distal surface 413 at a distal end 414 of the body 402. The proximal end 412 is spaced from the distal end 414 in a proximal direction P. The inner surface 410 defines a shaft channel 416 that extends along a central channel axis Cs through the body 402 from the proximal end 412 to the distal end 414. The inner surface 410 further defines a shaft retention portion 418. The shaft retention portion 418 is located toward the proximal end 412 of the body 402. The shaft retention portion 418 can include a locking feature 420 to at least temporarily secure the shaft 404 within the shaft channel 416. In an aspect, the locking feature 420 can include a threaded portion configured to engage with a corresponding body coupling element 434 of the shaft 404.

The body 402 further includes the holder fixation element 422 (e.g. a projection) configured to interface with the second aperture 356 of the bone plate 300. The holder fixation element 422 can extend distally from the distal surface 413. The holder fixation element 422 can have a substantially cylindrical shape, conical shape, or other shape. The shape and/or configuration of the holder fixation element 422 can correspond to a shape and/or configuration of the second aperture 356 of the bone plate 300. The interface between the holder fixation element 422 and the second aperture 356 facilitates alignment of the bone plate holder 400 with the bone plate 300. It will be appreciated that the body 402 can include multiple holder fixation elements 422, and the bone plate 300 can include multiple second apertures 356 that correspond to the multiple holder fixation elements 422.

Figure 17:
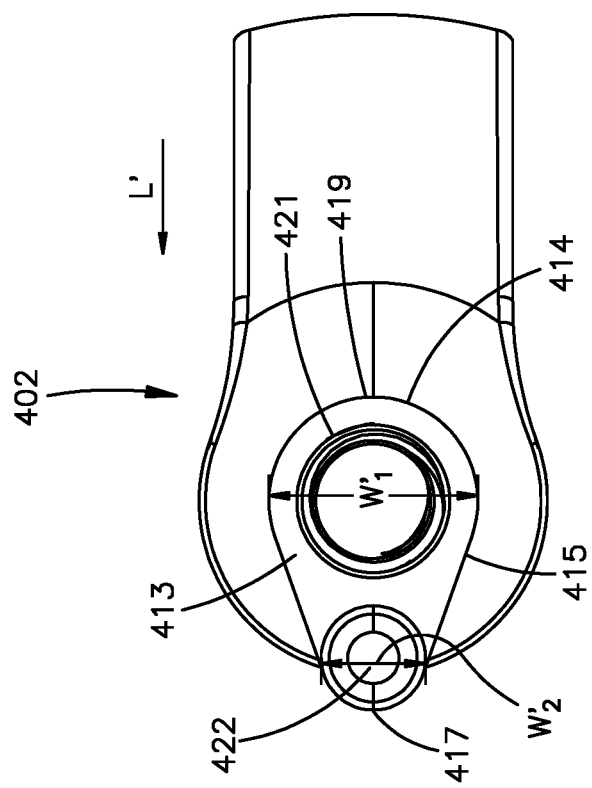
FIG. 17 illustrates a bottom view of the bone plate holder shown in FIG. 14.
Figure 20:
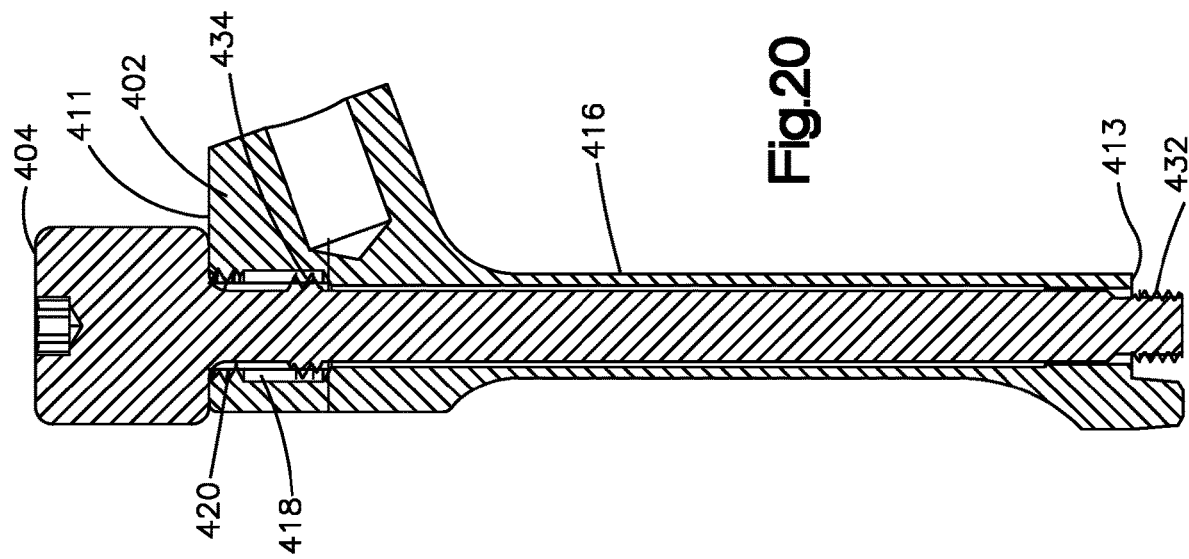
FIG. 20 illustrates a cross-sectional view of the shaft within the body shown in FIG. 19 taken along line 20-20.
Figure 19:
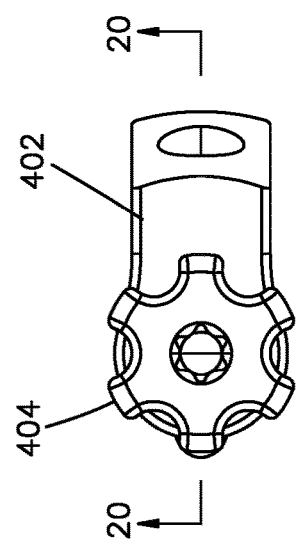
FIG. 19 illustrates a top view of the shaft within the body of the bone plate holder shown in FIG. 14.

Referring to FIG. 17, the distal surface 413 at the distal end 414 of the body 402 includes an outer edge 415 extending about a perimeter of the distal end 414. The outer edge 415 has a first end 417 spaced from a second end 419 in a lateral holder direction L'. The fixation element 422 is positioned between a distal opening 421 of the shaft channel 416 defined by the distal surface 413 and the first end 417 in the lateral holder direction L'. The distal opening 421 is positioned between the second end 419 and the fixation element 422 in the lateral holder direction L'. The outer edge 415 tapers in width, as measured in a direction substantially perpendicular to the lateral holder direction L', from a maximum width $W'_1$ of the outer edge 415 located toward the second end 419 to a minimum width $W'_2$ located toward the first end 417. A length between the maximum width W'$_1$ and the minimum width W'$_2$ along the outer edge 415 can be substantially linear.

A configuration of the distal end 414 of the body 402 can be configured to correspond to the recessed portion 352 of the fixation element 350 of the bone plate 300 so as to align the bone plate holder 400 with the bone plate 300 during connection of the holder 400 with the plate 300. For example, the distal end 414 of the body 402 can be received within the recessed portion 352 such that the plate lateral direction L aligns with the lateral holder direction L' to at least partially rotationally lock the holder 400 with the plate 300 while the shaft 404 of the holder 400 is being secured to the fixation element 350 of the plate 300. The maximum width W'$_2$ and the minimum width W'$_1$ of the outer edge 415 of the body 402 can be slightly less than the maximum width W$_2$ and the minimum width W$_1$ of the recessed portion 352, respectively, such that an outer surface 405 of the body 402 contacts an inner surface 351 of the recessed portion 352. The distal end 414 of the body 402 can be inserted into the recessed portion 352 of the plate 300 such that the distal surface 413 is substantially flush against the inner recessed surface 358.

Figure 18:
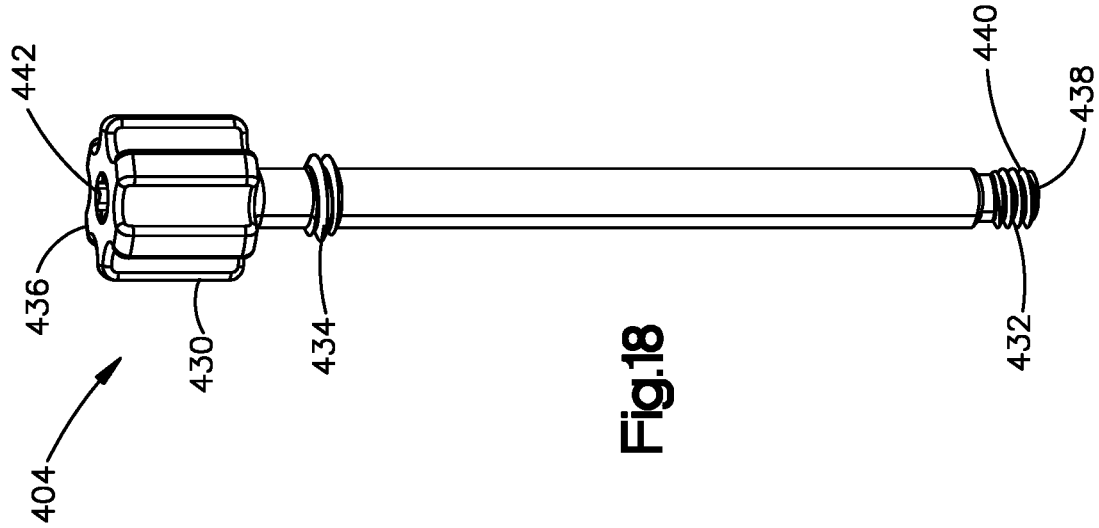
FIG. 18 illustrates a perspective view of a shaft of the bone plate holder shown in FIG. 14.

With reference to FIG. 18, the shaft 404 includes a control element 430 (e.g. a shaft grip member), the plate coupling element 432, and the body coupling element 434. The control element 430 is located at a proximal end 436 of the shaft 404. The plate coupling element 432 is located at a distal end 438 of the shaft 404. The body coupling element 434 is located between the plate coupling element 432 and the control element 430 along the shaft 404. The shaft 404 is configured to be inserted into the shaft channel 416 of the body 402 through the proximal end 412. The control element 430 can be positioned externally to the shaft channel 416, such that the control element 430 extends out of the proximal surface 411 of the body 402 in the proximal direction P and is accessible by a surgeon during a procedure. A distal surface of the control element 430 can abut against the proximal surface 411 of the body 402 when the shaft 404 is positioned within the shaft channel 416.

The plate coupling element 432 can extend through an opening defined by the distal end 414 of the body 402, such that the plate coupling element 432 extends distally out from the distal surface 413 of the body 402.

The body coupling element 434 is configured to engage with the locking feature 420 of the body 402. In an aspect, the body coupling element 434 can include a threaded portion configured to engage with a corresponding threaded portion of the locking feature 420. For example, during insertion of the shaft 404 into the shaft channel 416 of the body 402, the body coupling element 434 can engage the locking feature 420 until the body coupling element 434 is positioned distal to the locking feature 420. The position of the body coupling element 434 distal to the locking feature 420 can provide at least a temporary lock between the shaft 404 and the body 402, such that the shaft 404 is at least partially restricted from exiting the shaft channel 416 through the proximal end 412 of the body 402. For example, when the locking feature 420 and the body coupling element 434 are engaged and as the shaft 404 is rotated in a first direction of rotation (e.g. a clockwise direction), the body coupling element 434 moves distal to the locking feature 420 within the shaft retention portion 418. When the body coupling element 434 is in the position distal of the locking feature 420 of the body 402, the shaft 404 is then rotatable in the first direction of rotation without translating relative to the body 402.

The plate coupling element 432 is configured to connect with the first aperture 354 of the fixation element 350 of the bone plate 300. The plate coupling element 432 can include a threaded portion 440 that engages a corresponding threaded section of the first aperture 354. The shaft 404 can be rotated by rotating the control element 430 relative to the body 402 to threadedly connect the holder 400 to the bone plate 300. When the plate coupling element 432 is connected to the first aperture 354, and the holder fixation element 422 is connected to the second aperture 356, the bone plate holder 400 is rigidly received within the plate 300 such that linear and rotational movement between the holder 400 and the plate 300 is substantially prevented. The rigid connection between the holder 400 and the plate 300 allows the surgeon to control the movement and placement of the bone plate 300 relative to the bone 70 of the patient during a surgical procedure.

After the plate 300 is secured to the bone 70, the bone plate holder 400 can be removed from the bone plate 300. The shaft 404 can be disconnected from the first aperture 354 by rotating the control element 430 in a direction opposite to the direction of rotation for securing the plate coupling element 432 to the first aperture 354. After the plate coupling element 432 is disconnected, the holder 400 can be removed by retracting the distal end 414 of the body 402 from the recessed portion 352 and by retracting the holder fixation element 422 from the second aperture 356.

The control element 430 can include an engagement element 442 that defines a hexagonal or any alternatively shaped structure that can be engaged by a screw driving instrument, a protrusion element engageable by a wrench, or a cross hole configured to receive a cylindrical bar to rotate the control element 430 the bone plate holder 400 is being connected and disconnected to the plate 300.

Figure 21:
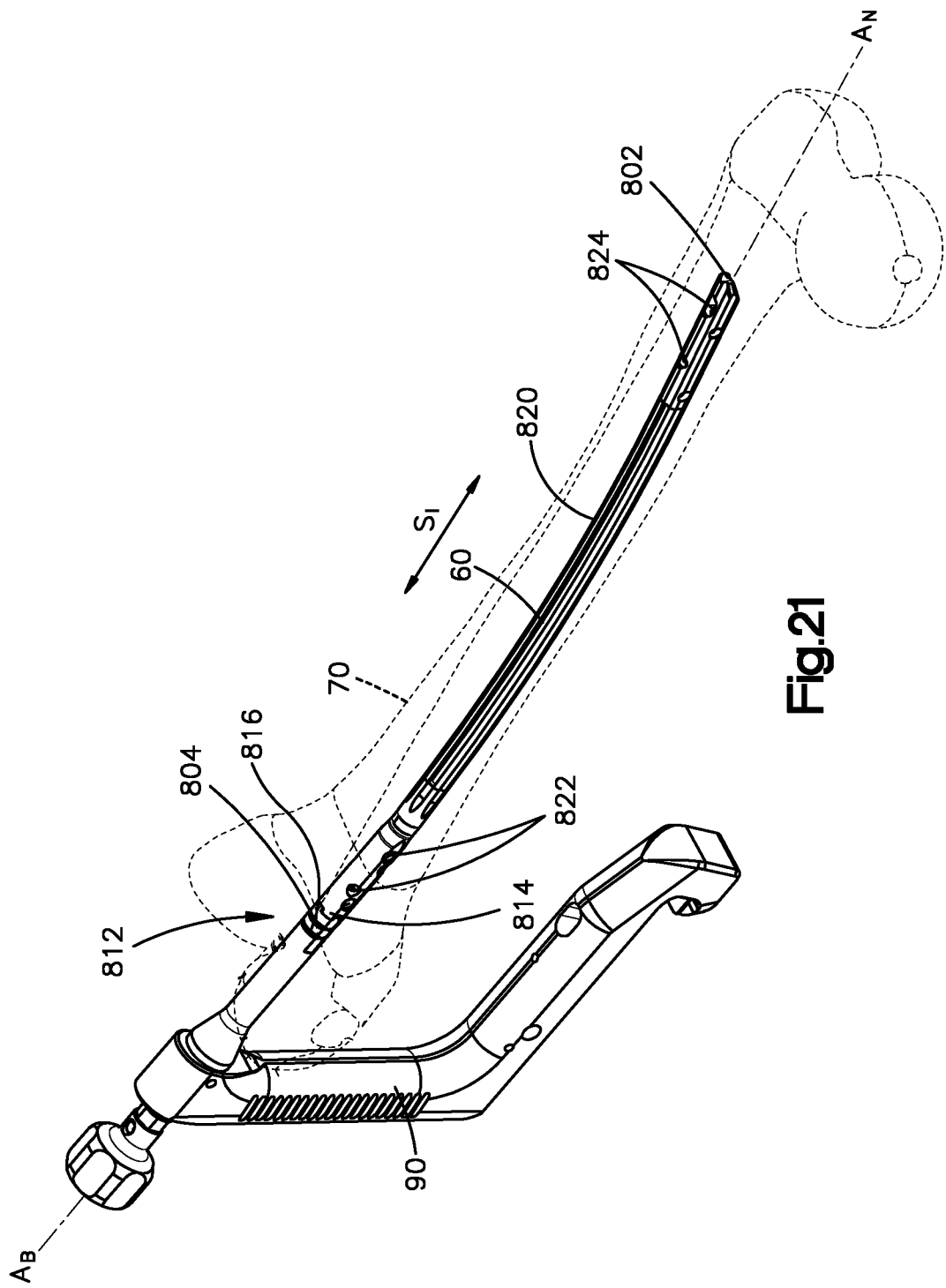
FIG. 21 illustrates a perspective view of an intramedullary nail that is received in medullary canal of a bone, the intramedullary nail coupled to a handle shown in FIG. 1.
Figure 22:
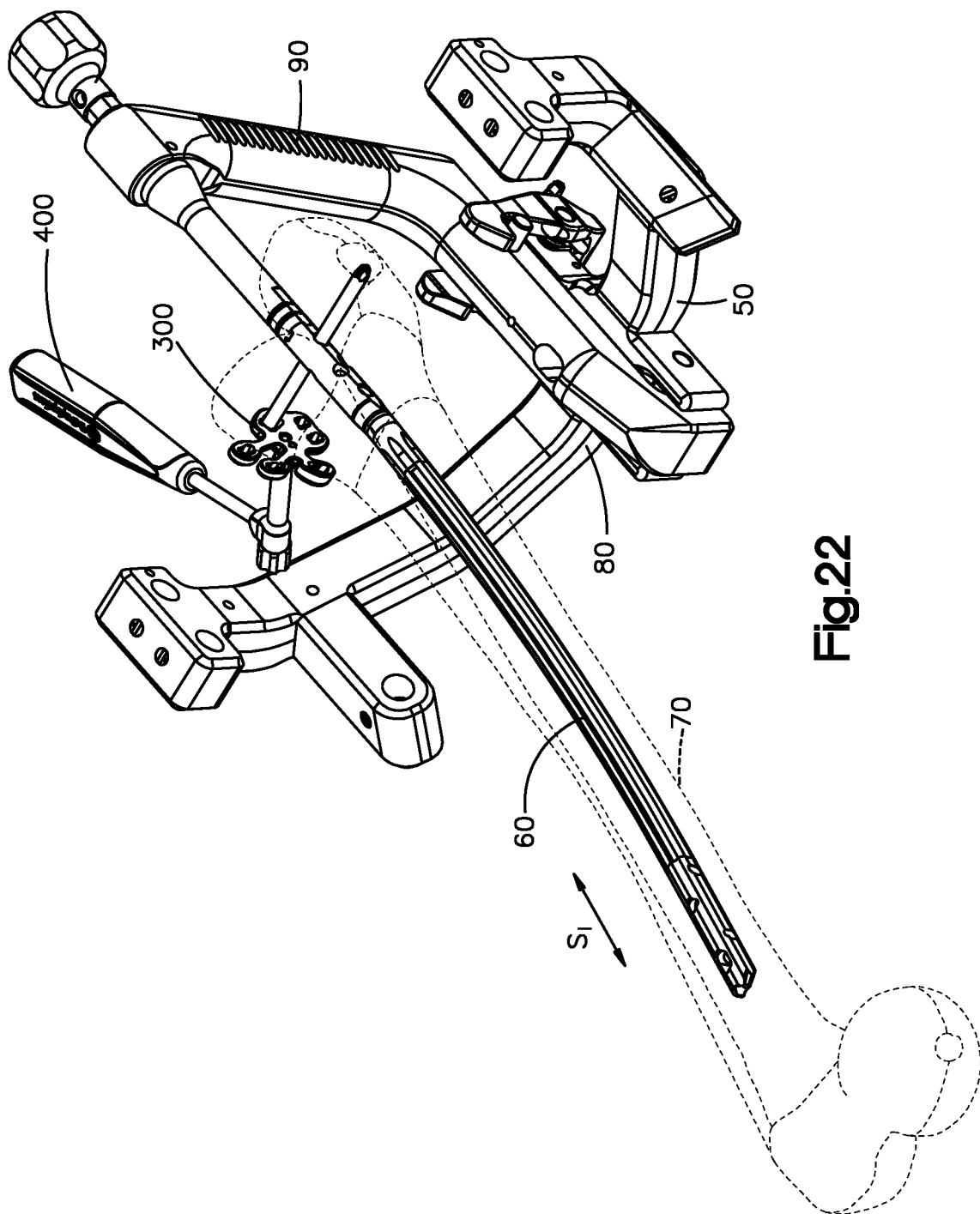
FIG. 22 illustrates a perspective view of a system comprising the intramedullary nail and handle as shown in FIG. 21 with an aiming guide and the bone plate holder shown in FIG. 14 fastened to the bone plate shown in FIG. 10.

With reference to FIGS. 21-26, an example embodiment of a method of implanting an intramedullary nail 60 will be described. As shown in FIG. 21, the handle 90 is coupled to the intramedullary nail 60, and the intramedullary nail 60 is driven into the medullary canal of the bone 70 by the handle 90. In FIG. 22, the aiming guide 80 of the aiming assembly 50 is fastened to the handle 90. The bone plate 300 is fastened to the bone plate holder 400 such that the bone plate 300 is configured to angulate with the plate holder 400 to position the bone plate 300 on the bone 70. Although reference is made below with respect to bone plate 300, it will be appreciated that the description also applies to bone plate 100 and/or other bone plate configurations.

The patient can be oriented so that anatomic lateral shows condylar overlap (e.g. perfect anatomic lateral), and the nail 60 can be rotated to a desired position (e.g. obtain perfect circles). The nail 60 can be locked to the bone 70 (e.g. distal fragment) with a bone screw. In an aspect, the initial screw to lock the nail 60 to the bone 70 is a medial oblique screw. The screw substantially prevents motion of the nail 60 relative to the bone 70.

Figure 23:
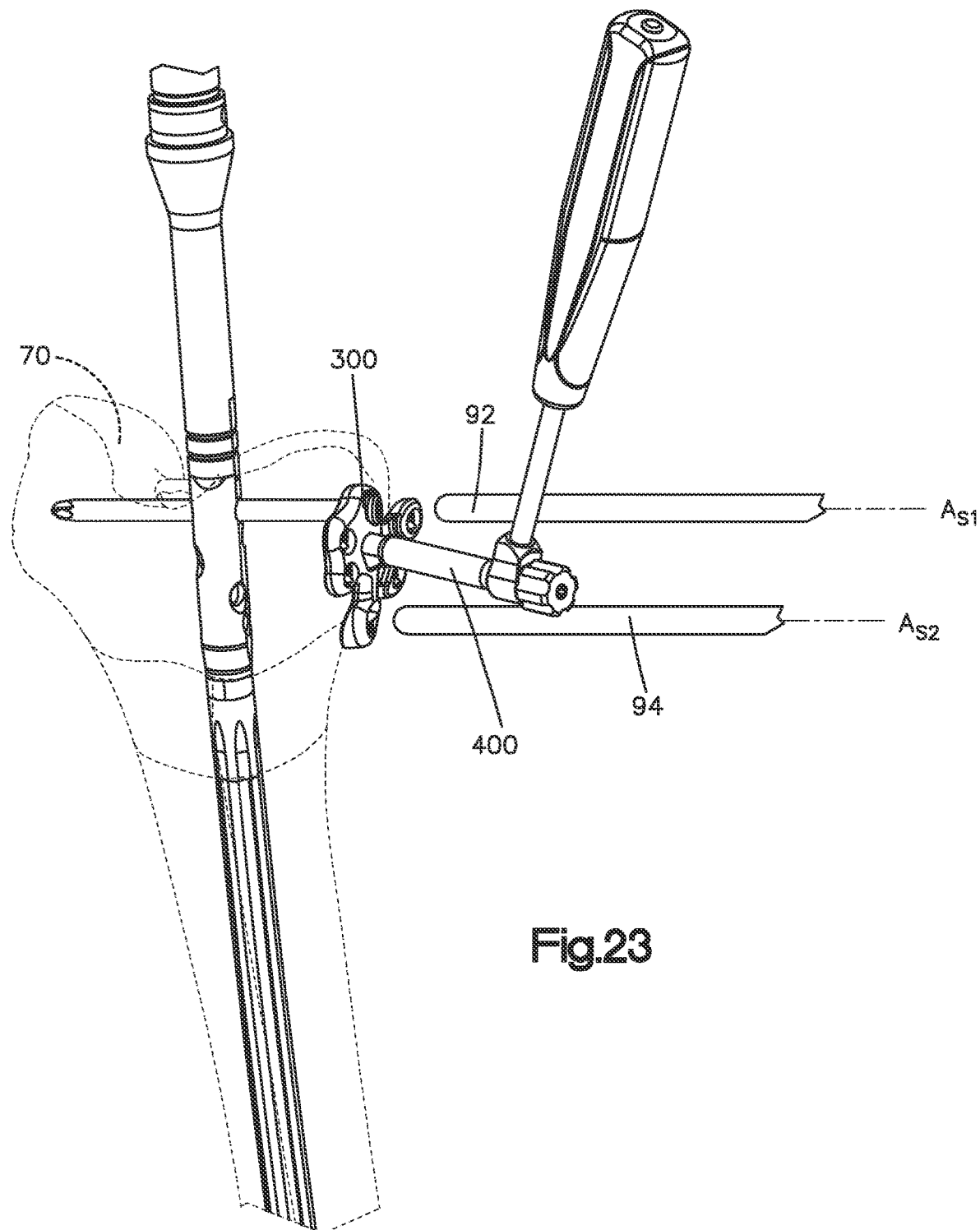
FIG. 23 illustrates a side view of the system of FIG. 22 with the bone plate holder supporting the bone plate and a pair of guide sleeves.

With reference to FIG. 23, an incision can be made and the bone plate 300 is introduced to the bone 70. The incision can include, for example, an 8 cm incision to connect first and second lateral guide sleeves 92 and 94. The first guide sleeve 92 can extend along the shaft longitudinal axis $A_{S1}$, and the second guide sleeve 94 can extend along a second longitudinal axis $A_{S2}$. The first guide sleeve 92 aligns with the first bone-anchor aperture 316 and a first aperture in the intramedullary nail 60, and the second guide sleeve 94 aligns with one of the additional bone-anchor apertures 318 and a second aperture in the nail 60. A first drill bit (not shown) can be inserted into one of the first and second guide sleeves 92 and 94 to drill a first hole in the bone 70. A second drill bit (not shown) can be inserted into the other of the first and second guide sleeves 92 and 94 to drill a second hole in the bone 70. One of the first and second drill bits is removed from the bone, and a first bone-anchor screw (e.g. 5.0 VA locking screw) is inserted into the hole. The first bone-anchor can be positioned such that the bone-anchor is approximately 1 cm proud. After the first bone-anchor has been inserted, a second bone-anchor screw (e.g. 5.0 VA locking screw) is inserted into the other hole formed. The second bone-anchor can be positioned such that the bone-anchor is approximately 1 cm proud.

After the first and second bone-anchors have been inserted, a lateral oblique bone-anchor screw can be inserted. After the first and second bone-anchors and the lateral oblique screw have been inserted, a lateral pressure can be applied to the plate 300 so the center and anterior portions of the plate 300 fit to the bone 70. This can push one or more of the tabs 330 off the bone 70. After the plate 300 is fit to the bone 70, the first and second bone-anchors are tightened. The bone plate holder 400 can be removed from the plate 300 by rotating the control element 430 to release the plate coupling element 432 of the shaft holder 400 from the first aperture 354 of the bone plate 300. The anterior locking screws can be inserted through the additional bone-anchor apertures 318. In an aspect, holes can be pre-drilled in the bone prior to inserting the anterior locking screws.

Figure 24:
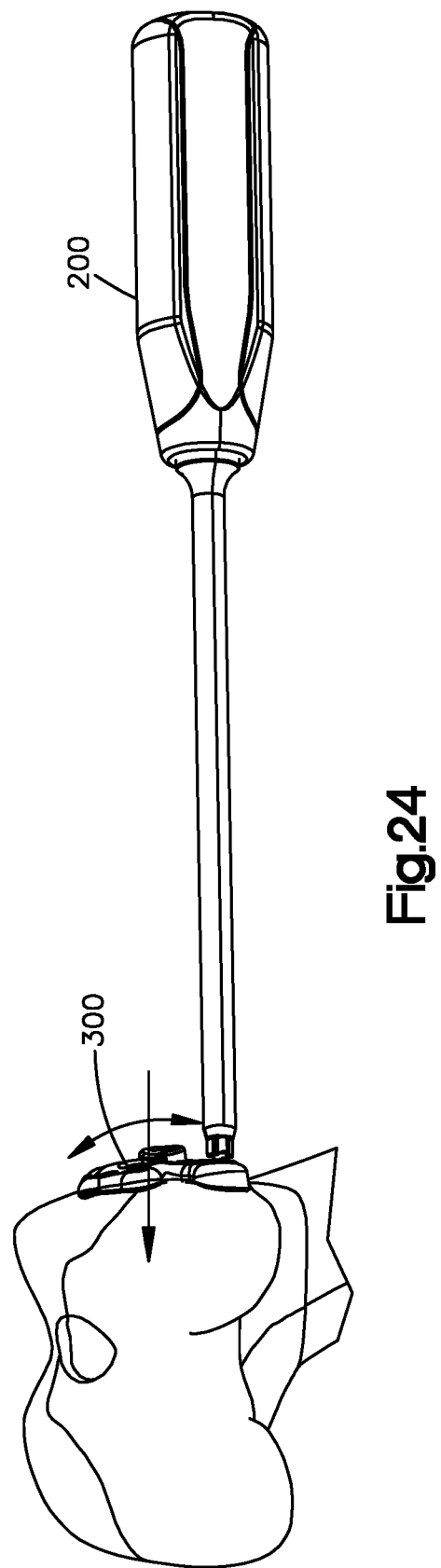
FIG. 24 illustrates a side view of the bone plate shown in FIG. 10 on a bone with the bone plate adjustment tool shown in FIG. 8 inserted into one of the tabs of the bone plate.
Figure 25:
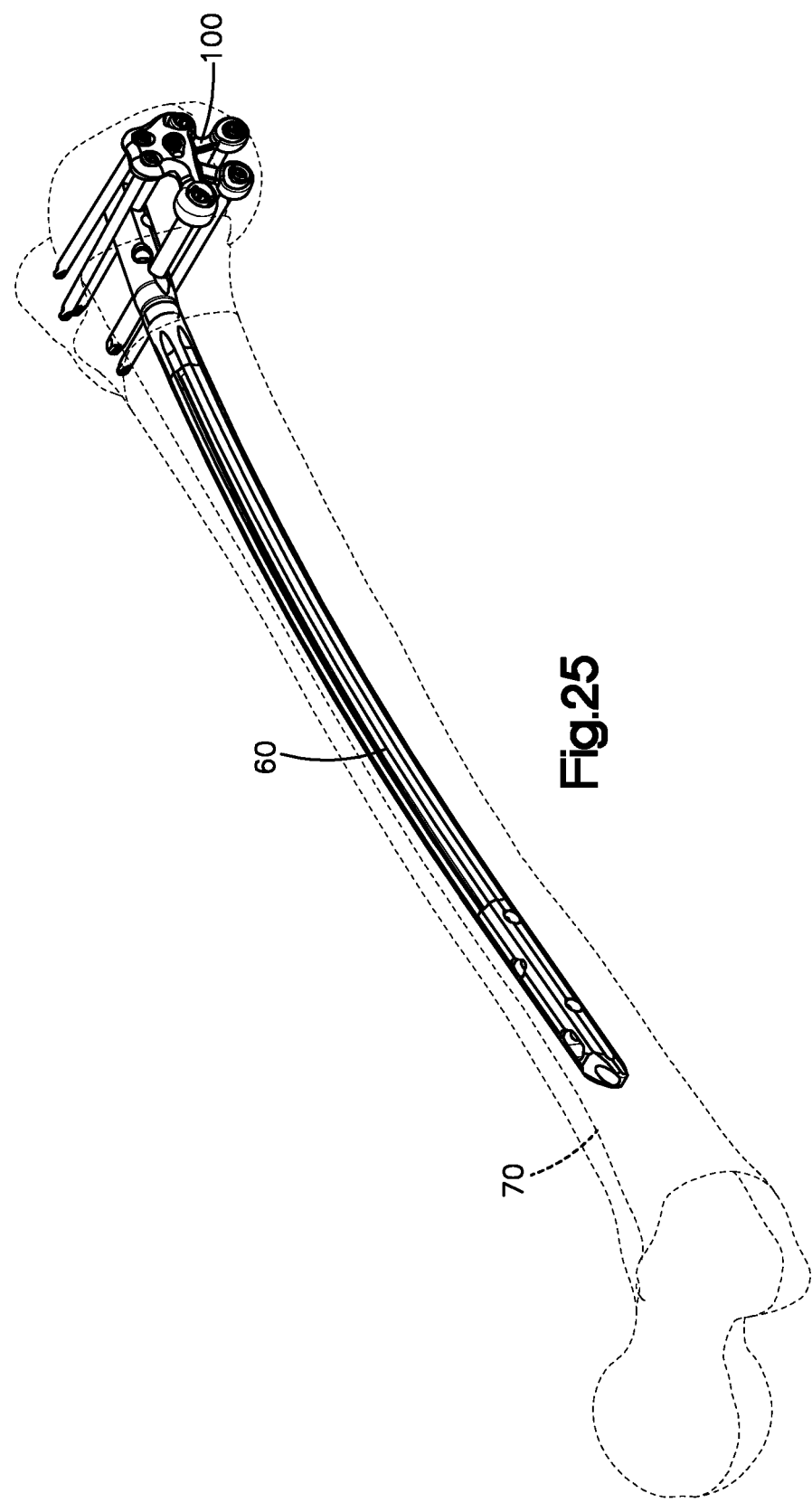
FIG. 25 illustrates a perspective view of the bone plate shown in FIG. 2 fastened to the intramedullary nail.
Figure 26:
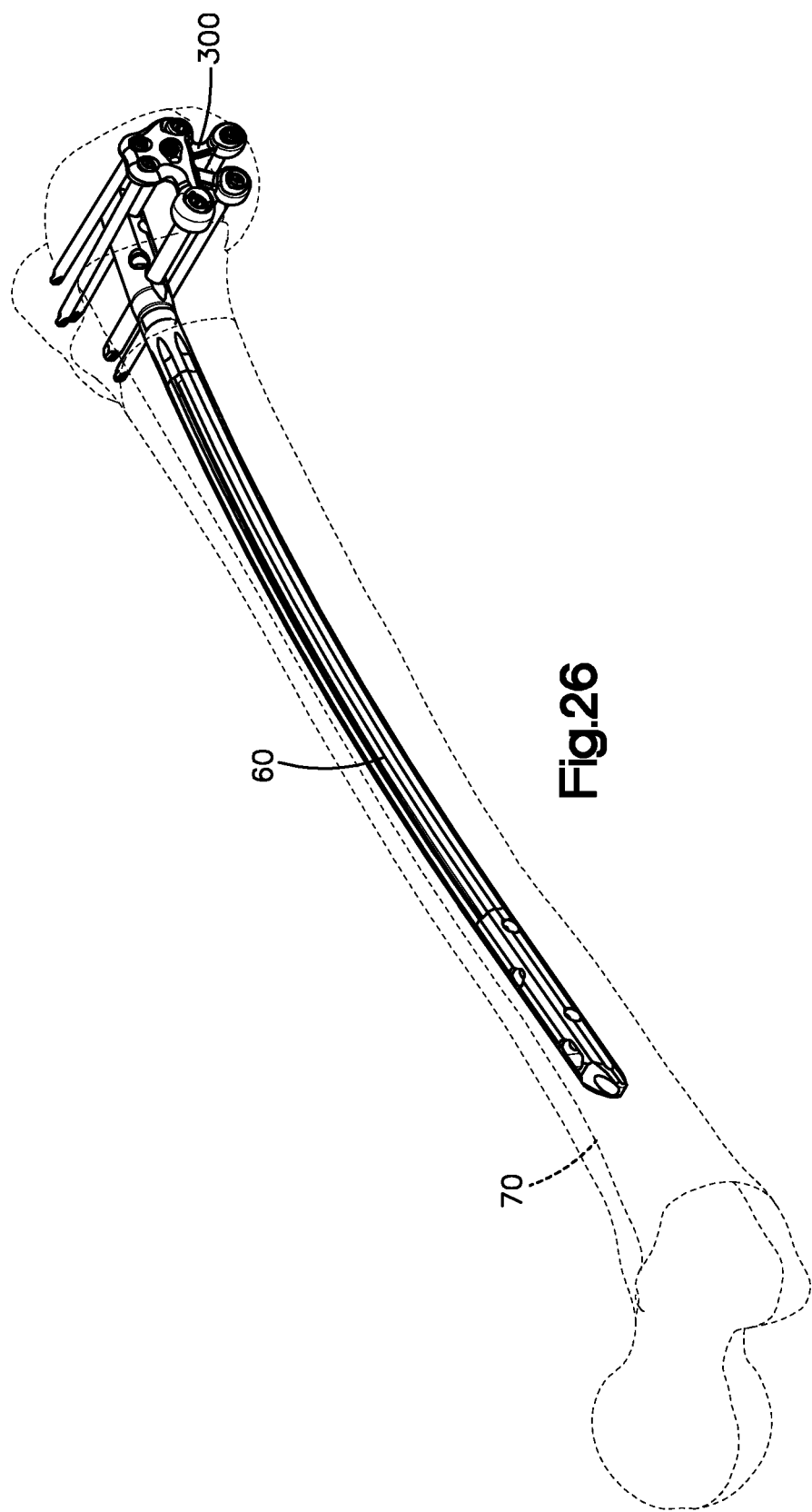
FIG. 26 illustrates a perspective view of the bone plate shown in FIG. 10 fastened to the intramedullary nail.

With reference to FIG. 24, the bone plate adjustment tool 200 can manipulate each of the at least one tab members 330 so that the posterior portions of the plate 300 fit to the bone 70. For example, the connection element 202 of the adjustment tool 200 is inserted into the respective aperture 336 of the tab 330, and a pressure (e.g. a deflection force) can be applied to the respective head 334 of the tab 330 to cause the arm 332 to deflect the head 334 from the pre-fixation position to the fixation position. For example, the arm 332 can deflect with respect to the plate body 301 in response to a force so as to move the head 334 between the pre-fixation position and the fixation position. The force applied to the arm 332 to transition the head between the pre-fixation position and the fixation position can be insufficient to cause the plate body 101 to deflect. After the head 334 is transitioned to the fixation position, the inner head surface 137 abuts the underlying bone. In an aspect, the arm 332 is deformable such that the fixation position of the head 334 is offset in the inward direction I with respect to the pre-fixation position of the head 334.

During transition, the trajectory of the screw through the respective aperture 336 should be considered to ensure the screw is securely located within the bone 70. After the tabs 330 have been transitioned to their respective fixation position, posterior bone-anchor screws can be inserted through each aperture 336 and into the bone 70. After each of the bone-anchors has been inserted, a final torque can be applied to the bone-anchors.

Although the disclosure has been described in detail, it should be understood that various changes, substitutions, and alterations can be made herein without departing from the spirit and scope of the invention as defined by the appended claims. Additionally, any of the embodiments disclosed herein can incorporate features disclosed with respect to any of the other embodiments disclosed herein. Moreover, the scope of the present disclosure is not intended to be limited to the particular embodiments described in the specification. As one of ordinary skill in the art will readily appreciate from that processes, machines, manufacture, composition of matter, means, methods, or steps, presently existing or later to be developed that perform substantially the same function or achieve substantially the same result as the corresponding embodiments described herein may be utilized according to the present disclosure.

What is claimed:

1. A bone plate comprising:
   a plate body that defines a bone-facing body surface and an outer body surface opposite the bone-facing body surface, wherein the bone plate defines a pair of threaded bone-anchor apertures that each extends through the plate body from the outer body surface to the bone-facing body surface, and the bone plate further defines additional first and second threaded bone-anchor apertures that extend through the plate body from the outer body surface to the bone-facing body surface, and
   first and second tabs each having a respective flexible arm that extends out from the plate body, and a respective head supported by the respective flexible arm, wherein 1) the first tab has only a single first tab aperture, and the single first tab aperture extends through the respective head of the first tab, 2) the second tab has only a single second tab aperture, and the single second tab aperture extends through the respective head of the second tab, and 3) each of the single first tab aperture and the second tab aperture is configured to receive a respective bone anchor;
   a third aperture that extends through the plate body from the outer body surface to the bone-facing body surface, the third aperture disposed such that 1) a first one of the pair of threaded bone-anchor apertures is offset in its entirety from the third aperture in a first direction, 2) a second one of the pair of threaded bone-anchor apertures is offset in its entirety from the third aperture in a second direction opposite the first direction, 3) each of the first and second threaded bone-anchor apertures are offset in their respective entireties from the third aperture in a third direction perpendicular to each of the first and second directions, and 4) the first and second single tab apertures are the only through holes of the bone plate that are offset in their respective entireties from the third aperture in a fourth direction opposite the third direction,
   wherein the pair of threaded bone-anchor apertures and the first and second threaded bone-anchor apertures extend through the plate body along respective central axes, and the each of the pair of threaded bone-anchor apertures is enlarged with respect to each of the first and second threaded bone-anchor apertures along respective directions perpendicular to the respective central axes.

2. The bone plate of claim 1, wherein the pair of bone-anchor apertures and the first and second bone-anchor apertures each defines variable-angle threading.

3. A system comprising:
   the bone plate of claim 1;
   a first bone anchor configured to threadedly mate with one of the pair of the threaded bone-anchor apertures and extend into bone; and
   a plurality of bone anchors configured to threadedly mate with the first and second threaded bone-anchor apertures, respectively.

4. The system of claim 3, further comprising an intramedullary nail having respective bone-anchor apertures configured to receive the first bone anchor and one of the plurality of bone anchors, respectively.

5. The system of claim 4, wherein another of the plurality of bone anchors are configured to be driven into bone.

6. The bone plate of claim 1, wherein the third aperture is threaded.

7. The bone plate of claim 1, wherein the third aperture is unthreaded.

8. The bone plate of claim 1, wherein the third aperture is disposed within a perimeter defined by the respective central axes of the pair of threaded bone-anchor apertures, the first and second threaded bone-anchor apertures, and further defined by respective central axes of the first and second single tab apertures.

9. The bone plate of claim 1, wherein the plate body further defines a recessed surface that surrounds the third aperture, wherein:
  i) the first one of the pair of threaded bone-anchor apertures is offset in its entirety from the recessed surface in the direction,
  ii) the second one of the pair of threaded bone-anchor apertures is offset in its entirety from the recessed surface in the second direction
  iii) each of the first and second threaded bone-anchor apertures are offset in their respective entireties from the recessed surface in the third direction; and
  the first and second single tab apertures are the only bone anchor apertures of the bone plate that are offset in their respective entireties from the recessed surface in the fourth direction.

10. The bone plate of claim 1, wherein each the flexible arms of the first and second tabs each has a respective inner bone-facing arm surface and an opposed outer arm surface, and each outer arm surface is inwardly recessed with respect to each of the outer body surface and the respective head.

11. A bone plate comprising:
  a plate body that defines an inner bone-facing body surface and an outer body surface opposite the bone-facing body surface, wherein the bone plate defines a plurality of threaded bone-anchor apertures that extend through the plate body from the outer body surface to the bone-facing body surface; and
  a tab having a flexible arm that extends out from the plate body, and a head supported by the flexible arm, the head defining an inner head surface configured to face bone and an outer head surface opposite the inner head surface, wherein the tab defines a tab aperture that extends through the head from the outer head surface to the inner head surface, the tab aperture configured to receive a bone anchor,
  wherein the flexible arm defines an inner bone-facing arm surface and an opposed outer arm surface, and the outer arm surface is inwardly recessed with respect to each of the outer body surface and the outer head surface.

12. The bone plate of claim 11, wherein the outer arm surface tapers out to the outer body surface.

13. The bone plate of claim 11, wherein the head defines a head thickness from the inner head surface to the outer head surface the plate body defines a body thickness from the inner bone-facing body surface and the outer body surface, and the head thickness is substantially equal to the body thickness.

14. The bone plate of claim 11, wherein the arm extends perpendicular to an outer perimeter of plate body.

15. The bone plate of claim 11, wherein the bone plate comprises a plurality of tabs each having a flexible arm that extends out from the plate body, and a head supported by the arm, and a tab aperture that extends through the head and is configured to receive a bone anchor, wherein each flexible arm defines a respective inner bone-facing arm surface and a respective opposed outer arm surface, and each outer arm surface is inwardly recessed with respect to the outer body surface.

16. A system comprising the bone plate of claim 11 and an intramedullary nail having respective bone-anchor apertures configured to receive first and second bone anchors that are threadedly mated to respective ones of the threaded bone-anchor apertures.

17. The system of claim 11, wherein the inner bone-facing arm surface is continuous with the inner bone-facing body surface.

* * * * *